US010307366B2

(12) United States Patent
Brumbaugh et al.

(10) Patent No.: US 10,307,366 B2
(45) Date of Patent: Jun. 4, 2019

(54) COMPOSITION AND RELATED METHOD FOR INHIBITING MOISTURE LOSS FROM SKIN

(71) Applicant: Access Business Group International LLC, Ada, MI (US)

(72) Inventors: Ernest H. Brumbaugh, Rockford, MI (US); Hilary Cadeau Kindt, Columbus, WI (US); Kelly M. Glynn, Grand Rapids, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 0 days.

(21) Appl. No.: 15/447,634

(22) Filed: Mar. 2, 2017

(65) Prior Publication Data

US 2017/0252293 A1 Sep. 7, 2017

Related U.S. Application Data

(60) Provisional application No. 62/302,972, filed on Mar. 3, 2016.

(51) Int. Cl.
*A61K 8/98* (2006.01)
*A61K 8/60* (2006.01)
(Continued)

(52) U.S. Cl.
CPC ............... *A61K 8/988* (2013.01); *A61K 8/04* (2013.01); *A61K 8/345* (2013.01); *A61K 8/602* (2013.01);
(Continued)

(58) Field of Classification Search
None
See application file for complete search history.

(56) References Cited

U.S. PATENT DOCUMENTS 5,965,145 A 10/1999 Marion et al.
7,364,759 B2 4/2008 Leverett et al.
(Continued)

FOREIGN PATENT DOCUMENTS

DE 102008008426 A1 8/2009
FR 2784579 A1 4/2000
(Continued)

OTHER PUBLICATIONS

Naked Bee Moisturizing Hand & Body Lotion, ([retrieved from on-line website: https://www.amazon.com/Naked-Bee-Moisturizing-Lotion-Blossom/dp/B00117CH5M/ref=pd_sm_121_2?_encoding=UTF8&pd_rd_i=B00117CH5M&pd_rd_r=VE4FCN6E7GTC055YCHH4&pd_rd_w=woxTu&pd_rd_wg=C97in&refRID=VE4FCN6E7GTC055YCHH4&th=1]) (Year: 2014).*
(Continued)

*Primary Examiner* — Ernst V Arnold
*Assistant Examiner* — Kyung S Chang
(74) *Attorney, Agent, or Firm* — Warner Norcross & Judd LLP

(57) ABSTRACT

A method useful for inhibiting moisture loss from skin comprises the step of administering a composition to a subject's skin. The composition comprises a first humectant and a second humectant different from the first humectant. The humectants are useful for increasing moisture content of the subject's skin, specifically the subject's epidermis. The first humectant may comprise a conventional humectant, e.g. glycerol. The second humectant generally comprises certain types of honey. The honey is capable of inhibiting moisture loss from the subject's epidermis and/or moisture loss from the first humectant when the subject is exposed to dry air conditions, e.g. wintertime air having a relative humidity of about 50% or less. Specifically, the second humectant is useful for mitigating adverse effects of the first humectant
(Continued)

under certain conditions. Examples of suitable honeys generally include those comprising the flavanone hesperidin, such as orange blossom honey, buckwheat (blossom) honey, or a combination thereof.

20 Claims, 6 Drawing Sheets

(51) Int. Cl.
    *C11D 17/00*     (2006.01)
    *A61K 8/34*     (2006.01)
    *A61Q 19/10*     (2006.01)
    *A61K 8/02*     (2006.01)
    *A61Q 19/00*     (2006.01)
    *A61K 8/04*     (2006.01)
    *A61Q 15/00*     (2006.01)

(52) U.S. Cl.
    CPC .............. *A61Q 15/00* (2013.01); *A61Q 19/00* (2013.01); *A61Q 19/007* (2013.01); *A61Q 19/10* (2013.01); *C11D 17/0047* (2013.01); *A61K 2800/30* (2013.01)

(56) References Cited

U.S. PATENT DOCUMENTS

| | | |
|---|---|---|
| 7,897,184 B1 | 3/2011 | Rana et al. |
| 8,623,335 B2 | 1/2014 | Waddington |
| 2011/0300083 A1 | 12/2011 | Yontz et al. |
| 2013/0302265 A1 | 11/2013 | Rana et al. |
| 2015/0064124 A1 | 3/2015 | Yontz et al. |
| 2016/0367605 A1 | 12/2016 | Quero et al. |

FOREIGN PATENT DOCUMENTS

| | | |
|---|---|---|
| FR | 3007291 A1 | 12/2014 |
| WO | WO2013004953 A2 | 1/2013 |
| WO | WO2015198196 A9 | 12/2015 |

OTHER PUBLICATIONS

Ferreres et al., "Hesperetin: a marker of the floral origin of citrus honey", J Sci Food Agri 1993, 61, pp. 121-123. (Year: 1993).*

Orange Blossom Honey, Carmel Honey Company ([retrieved from on-line website: https://web.archive.org/web/20161023052316/https://carmelhoneycompany.com/products/orange-blossom-honey, Oct. 23, 2016 on-line available]), (Year: 2016).*

English language abstract and Machine Translation for DE102008008426 (A1) extracted from http://worldwide.espacenet.com database on May 24, 2017,11 pages.

English language abstract and Machine Translation for WO2013004953 (A2) extracted from http://worldwide.espacenet.com database on May 24, 2017,31 pages.

PCT/US2017/020312 International Search Report dated May 17, 2017, 6 pages.

Ni Cheng, Liming Wu, Jianbin Zheng, and Wei Cao, "Buckwheat Honey Attenuates Carbon Tetrachloride-Induced Liver and DNA Damage in Mice", Research Article, Department of Food Science and Engineering School of Chemical Engineering, Northwest University, Xian, China, 2015, 10 pages.

Isabel Escriche, Melinda Kadar, Marisol Juan-Borras, and Eva Domenech, "Using flavonoids, phenolic compounds and headspace volatile profile for botanical authentication of lemon and orange honeys", Food Research International, Spain, Mar. 23, 2011, 10 pages.

Bruno Burlando, PHD and Laura Cornara, MSC, "Honey in dermatology and skin care: a review", Journal of Cosmetic Dermatology, Italy, vol. 12, pp. 306-313, 7 pages.

Basf, "The Honey-Moisturizer Optimal ecological hydro-regulation", Melhydran LS 9876, France, Jul. 2015, 4 pages.

"Honey Chemical Composition, Characterization, and Differentiation in Advances in Food and Nutrition Research", Jan. 1, 2011, 1 page.

English language abstract and Machine Translation for FR2784579 (A1) extracted from http://worldwide.espacenet.com database on Jun. 1, 2017,5 pages.

* cited by examiner

COMPOSITION AND RELATED METHOD FOR INHIBITING MOISTURE LOSS FROM SKIN

CROSS-REFERENCE TO RELATED APPLICATIONS

This application claims priority to and all advantages of U.S. Patent Application No. 62/302,972 filed on 3 Mar. 2016, the content of which is hereby incorporated by reference.

FIELD OF THE INVENTION

The present invention generally relates to a method for inhibiting moisture loss from skin of a subject, especially under dry air (e.g. low humidity) conditions. The method comprises the step of administering a composition to the subject's skin. The composition comprises a first humectant and a second humectant different from the first humectant. The first humectant may be a conventional humectant. The second humectant comprises honey and/or certain compounds derived from honey that mitigates adverse effects of the first humectant under low humidity or dry air conditions.

DESCRIPTION OF THE RELATED ART

Many skin care products, such as cosmetic moisturizers, improve the condition of dry skin by utilizing a number of conventional ingredients including humectants and occlusive agents. Humectants are frequently used as a way of increasing and maintaining moisture in the skin.

As hygroscopic moisturizers, humectants function by attracting water to the upper layer of the skin (i.e., the stratum corneum of the epidermis). Humectants have hydrophilic (e.g. hydroxyl) groups which allow them to participate in hydrogen bonding and attract water. This process attracts moisture from the outer layer of the skin or, in high humidity air, from the atmosphere. The moisture is then trapped against the epidermis. Unfortunately, utilizing high levels of humectants can cause undesirable aesthetics, such as tackiness. Moreover, when humectants are used in low humidity air, such as in late winter or early spring, they will often draw moisture away from the skin itself thus causing undesirable dryness.

To mitigate such dryness issues, occlusive agents are often used in conjunction with humectants. Occlusive agents increase moisture levels in skin by providing a physical barrier (e.g. a film) to impede epidermal water loss. Unfortunately, occlusive agents can leave a heavy feeling on skin and/or cause undesirable aesthetics, such as tackiness or greasiness. Moreover, occlusive agents can impede humectants from drawing in moisture to begin with. For example, occlusive agents can seal in what water is already present in the skin, but prevent the uptake of additional moisture from the atmosphere.

In view of the foregoing, there remains an opportunity to provide improved methods of addressing dry skin conditions. There also remains an opportunity to provide improved compositions for addressing dry skin conditions.

SUMMARY OF THE INVENTION

A method is provided that is useful for inhibiting moisture loss from skin. The method comprises the step of administering a composition to a subject's skin. The composition comprises a first humectant and a second humectant different from the first humectant. The humectants are useful for increasing moisture content of the subject's skin, specifically the subject's epidermis. The second humectant comprises honey and/or honey compounds. The honey is capable of inhibiting moisture loss from the subject's epidermis and/or moisture loss from the first humectant when the subject is exposed to dry air conditions.

In various embodiments, the first humectant comprises glycerol. The second humectant comprises certain types of honey, such as orange blossom honey and/or buckwheat honey. Surprisingly, the inventors discovered that certain types of honey work well to mitigate the detrimental effect of humectants, such as glycerol, under dry air conditions.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE INVENTION

Figure 1:
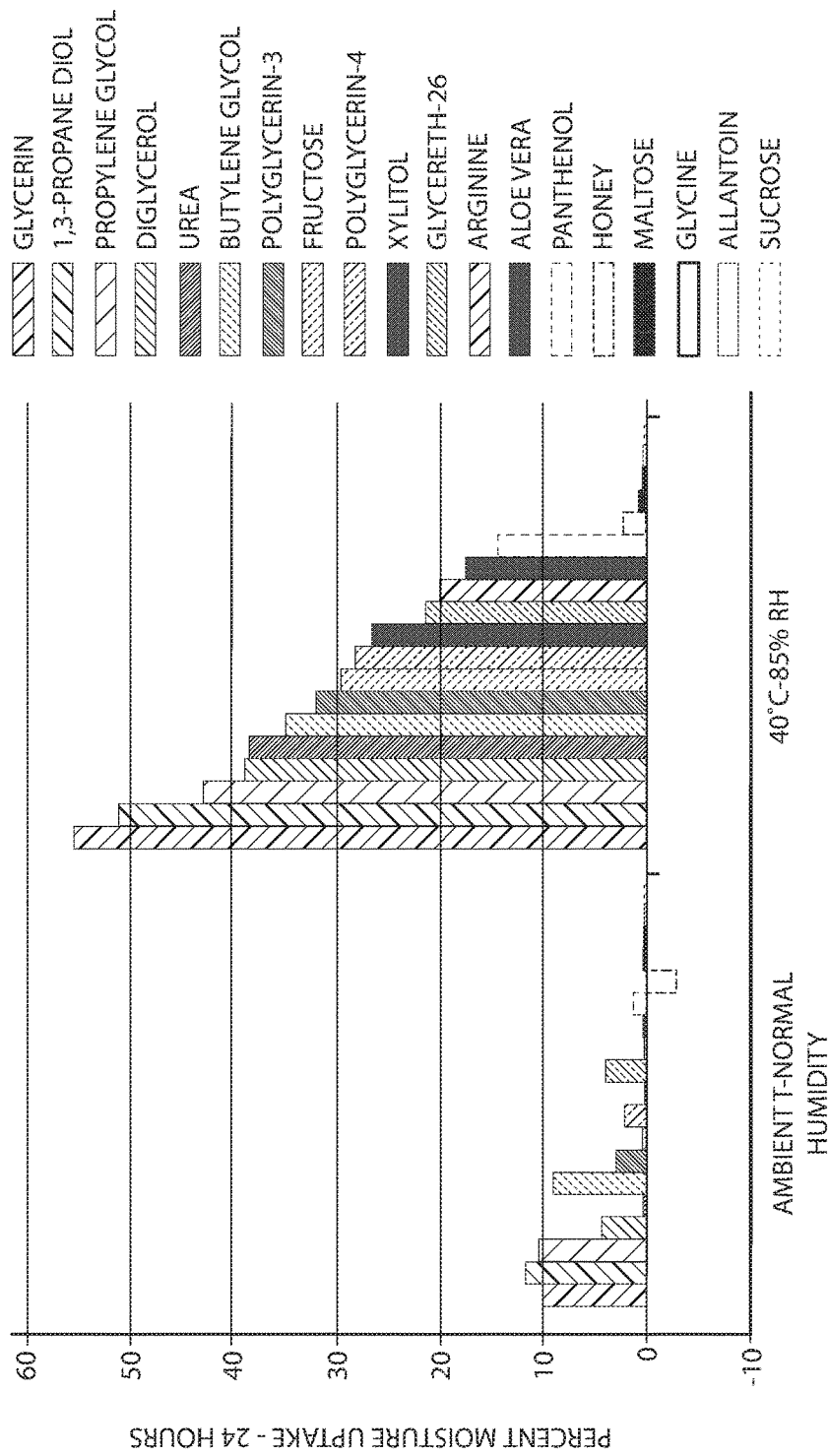
FIG. 1 is a graph illustrating moisture uptake of conventional humectants often utilized in personal care compositions.

The method herein is useful for inhibiting moisture loss from skin. In addition, the method can be useful for moisturizing the skin and/or addressing other desirable outcomes. The method of this disclosure may be referred to as a cosmetic method or as a treatment method. The method may also be referred to as a method of mitigating cytotoxic effects of humectants on skin cells. In particular, the method may also be referred to as a method of mitigating adverse effects of conventional humectants.

The method comprises the step of administering a composition to a subject's skin. Typically, the composition is applied by hand; however, the composition can also be applied via an application means directly or indirectly to the skin, e.g. via an applicator, nozzle, patch, etc. The composition of this disclosure may be referred to as a personal care composition, skincare composition, topical composition, or cosmetic composition.

The composition may be administered as needed, daily, several times per day or in any suitable regimen such that the desired outcome is achieved. In the method, the frequency of application can depend on several factors, including the desired level of preventing moisture loss and/or addressing dryness. Generally, a regimen includes application of the composition to the skin once or twice daily to include an application in the morning and/or an application in the evening. The amount of composition applied to the skin during each application may depend on several factors including level of desired results and the specific composition.

The subject is typically mammalian, more typically a human, and can include males and females of various ages. The composition is not limited to a particular subject or location of skin on the subject. For example, a person may apply the composition to their face, neck, arms, hands, chest, torso, legs, feet, etc., or any combination thereof. Such skin areas may be normal, dry, sensitive, oily, or combinations thereof.

The composition comprises a first humectant and a second humectant different from the first humectant. The composition may include one or more additional components as described herein, such as an additional humectant (different from the first and second) and/or one or more additives. In various embodiments, the composition consists essentially of the first and second humectants. As used herein, the phrase "consisting essentially of" generally encompasses the specifically recited elements/components for a particular embodiment. Further, the phrase "consisting essentially of" generally encompasses and allows for the presence of additional or optional elements/components that do not materially impact the basic and/or novel characteristics of that particular embodiment. In certain embodiments, "consisting essentially of" allows for the presence of ≤10, ≤5, or ≤1, weight percent (wt. %) of additional or optional components based on the total weight of the composition. In other embodiments, the composition consists of the first and second humectants as described herein. The first and second humectants are described further below, along with optional components of the composition and additional aspects thereof. It is to be appreciated that the terms "first" and "second" are not to be construed as requiring a particular order or indicating a particular importance of one humectant relative to the other.

Each of the first and second humectants generally is useful for increasing moisture content of the subject's epidermis. Humectants generally add moisture by drawing water molecules from the environment towards the epidermis in order to help re-hydrate the skin's surface. They help to increase the amount of water within the skin and store it away until it is needed, making humectants a great moisturizer for the majority of skin types, including normal, dry, oily, and combination skin.

Moreover, the second humectant is capable of inhibiting moisture loss from the subject's epidermis and/or moisture loss caused by or due to the first humectant when the subject is exposed to dry air conditions. As used herein, the phrase "dry air" or "dry air conditions" generally encompasses air having a relative humidity (RH) of optionally no greater than about 50%, optionally no greater than about 45%, optionally no greater than about 40%, optionally no greater than about 35%, optionally no greater than about 30%, optionally no greater than about 25%, optionally no greater than about 20%, optionally no greater than about 15%, or optionally no greater than about 10%. Such dry air conditions are often encountered between late fall and early spring, and more often during winter.

First Humectant

The first humectant may be any type of humectant understood in the art. Examples of suitable humectants include, but are not limited to, glycerin, hyaluronic acid, sorbitol, urea, alpha hydroxy acids, sugars, lactic acid, propylene glycol, glyceryl triacetate, lithium chloride, polyols like sorbitol, xylitol and maltitol, polymeric polyols like polydextrose, natural extracts like quillaia, hexadecyl, myristyl, isodecyl and isopropyl esters of adipic, lactic, oleic, stearic, isostearic, myristic and linoleic acids, as well as many of their corresponding alcohol esters (e.g. sodium isostearoyl-2-lactylate, sodium capryl lactylate), hydrolyzed protein and other collagen-derived proteins, aloe vera gel, acetamide monoethanolamide (MEA), compounds found to be naturally occurring in the stratum corneum of the skin such as sodium pyrrolidone carboxylic acid, lactic acid, urea, L-proline, guanidine and pyrrolidone, acetamide MEA, acetamido propyl trimonium chloride, calcium stearoyl lactylate, chitosan pyrrolidone carboxylic acid (PCA), diglycerol lactate, ethyl ester of hydrolyzed silk, fatty quaternary amine chloride complex, glycereth-7, glycereth-12, glycereth-26, glycereth-4.5 lactate, glycerin, diglycerin, polyglycerin, hydrolyzed fibronectin, lactamide MEA, lactamide N-(2-hydroxyetheryl), mannitol, methyl gluceth-10, methyl gluceth-20, methylsilanol PCA, panthenol, PCA, polyethylene glycol (PEG), PEG-4, PEG-8, polyamino sugar condensate, quaternium-22, sea salts, sodium capryllactylate, sodium hyaluronate, sodium isostearoyl lactylate, sodium lactate, sodiumlauroyl lactylate, sodium PCA, sodium polyglutamate, sodium stearoyl lactylate, soluble collagen, sorbitan laurate, sorbitan oleate, sorbitan sesquiisostearate, sorbitan stearate, sorbitol, sphingolipids, TEA-PCA, ethylene glycol, diethylene glycol, triethylene glycol, and other polyethylene glycols, propylene glycol, dipropylene glycol and other propylene glycols, 1,3-butylene glycol, 1,4-butylene glycol and other butylene glycols, glycerol, diglycerol and other polyglycerols, mannitol, xylitol, maltitol and other sugar alcohols, glycerol ethylene oxide (EO) and propylene oxide (PO) adducts, sugar alcohol EO and PO adducts, adducts of EO or PO and monosaccharides such as galactose and fructose, adducts of EO or PO and polysaccharides such as maltose and lactose, sodium pyrrolidonecarboxylate, polyoxyethylene methyl glycoside, polyethylene glycol, propylene glycol, dipropylene glycol, 1,3-butylene glycol, hexylene glycol, xylitol, maltitol, maltose, D-mannitol, gluten, glucose, fructose, lactose, sodium chondroitin sulfate, sodium hyalonate, sodium adenosine phosphate, gallates, pyrrolidone carbonates, glucosamine, cyclodextrin, alpha hydroxy acids, 2-methyl-1,3-propane diol, or combinations thereof. Suitable humectants are commercially available from a number of suppliers.

In various embodiments, the first humectant comprises a sugar alcohol, optionally the first humectant comprises glycerol. Glycerol (also called glycerine or glycerin) is a simple polyol (sugar alcohol) compound. Glycerol has three hydroxyl groups that are responsible for its solubility in water and its hygroscopic nature. The glycerol backbone is central to all lipids known as triglycerides. Glycerol's IUPAC name is propane-1,2,3-triol. In certain embodiments, the first humectant consists essentially of glycerol, optionally consists of glycerol. The glycerol may be natural or synthetic, optionally naturally derived from plants and/or animals, or optionally naturally derived from plants (e.g. soybeans, palm, etc.). Other than serving as a humectant in the composition, glycerol can also be useful for improving smoothness and providing lubrication. In specific embodiments, the first humectant comprises USP Glycerin.

The first humectant may be present in the composition in various amounts. In various embodiments, the first humectant is present in an amount of from about 0.001 to about 99.999, optionally of from about 0.01 to about 99.99, optionally of from about 0.1 to about 99.9, optionally of from about 1 to about 99, optionally of from about 5 to about 95, optionally of from about 10 to about 90, optionally of from about 15 to about 85, optionally of from about 20 to about 80, optionally of from about 25 to about 75, optionally of from about 30 to about 70, optionally of from about 35 to about 65, optionally of from about 40 to about 60, optionally of from about 45 to about 55, or optionally about 50, parts by weight, based on 100 parts by weight of the composition. It is contemplated that any and all values or ranges of values between those described above may also be utilized. Such amounts are generally based on the composition including the second humectant, and can be normalized to account for the inclusion of one or more additional components.

Second Humectant

As introduced above, the second humectant is different from the first humectant. Typically, the humectants are chemically different rather than just physically different, although they can be both chemically and physically different.

The second humectant comprises honey. The term "honey" may encompass one or two or more types of honey. The honey is capable of inhibiting moisture loss from the subject's epidermis and/or moisture loss from the first humectant when the subject is exposed to dry air conditions. As understood in the art, honey is a natural humectant, i.e., it attracts and retains moisture. Surprisingly, as reinforced in the EXAMPLES section below, the inventors discovered a synergistic effect between the first and second humectants in this regard, especially with certain types of honey described herein. In certain embodiments, the second humectant consists essentially of honey, optionally consists of honey.

Honey is made by bees that collect nectar from flowers of plant types. The variety produced by honey bees (the genus *Apis*) is the one most commonly referred to, as it is the type of honey collected by most beekeepers and consumed by people. Honeys are also produced by bumblebees, stingless bees, and other hymenopteran insects such as honey wasps, though the quantity is generally lower and they have slightly different properties compared to honey from the genus *Apis*. Honey bees convert nectar into honey by a process of regurgitation and evaporation. They store it as a primary food source in wax honeycombs inside the beehive. Honey is collected from wild bee colonies, or more often from domesticated beehives.

The honeycomb is removed from the hive and the honey may be extracted from that, typically either by crushing or by using a honey extractor. The honey is then usually filtered to remove beeswax and other debris. In various embodiments, the honey is selected from the group of raw honey, strained honey, filtered honey, ultra-sonicated honey, or combinations thereof. In certain embodiments, the honey is pasteurized or unpasteurized, optionally unpasteurized. It is thought that heating, such as pasteurization, may destroy certain aspects of honey (e.g. enzymes, minerals and/or vitamins). Honey generally includes the enzyme glucose oxidase, which produces hydrogen peroxide when combined with water. This may be useful for preventing or treating certain skin conditions.

Honey also includes a number of flavonoid markers including at least one of quercetin, hesperidin, hesperetin, and chrysin. Hesperidin is a flavanone glycoside found in citrus fruits. Its aglycone form is called hesperetin. It is believed that hesperetin is produced by hydrolysis of hesperidin by the bee enzymes present in honey. Hesperidin may also be referred to as Vitamin P. In various embodiments, the honey comprises the flavanone hesperidin, optionally the flavanone hesperetin-7-rutinoside.

In various embodiments, the honey comprises, optionally is, a monofloral honey. As understood in the art, monofloral honeys are generally derived from a single plant source, e.g. nectar of one plant type, rather than nectar from different plant types (e.g. of different genus and/or species). In certain embodiments described immediately below, the honey comprises citrus honey, buckwheat honey, or a combination thereof.

Citrus Honey

In various embodiments, the second humectant/honey comprises citrus honey. This type of honey is derived from nectar of citrus trees. All citrus trees belong to the single genus *Citrus* and remain almost entirely interfertile. This means that there is only one superspecies that includes grapefruits, lemons, limes, oranges, and various other types and hybrids. Different names have been given to the many varieties of the genus.

The scientific classification for citrus trees is generally as follows—Order: Sapindales; Family: Rutaceae; and Genera: *Citrus* L. Hybrids between two or more species of *Citrus* may also be possible. In various embodiments, the citrus honey source can be selected from one or more of the *Citrus* species. In various embodiments, the honey comprises citrus honey and a majority of the honey is derived from blossoms (or flowers) of the genus *Citrus*, optionally from blossoms of the species *Citrus sinensis*. In certain embodiments, the second humectant consists essentially of citrus honey, optionally consists of citrus honey. Other than serving as a humectant in the composition, citrus honey mitigates drying effects of the first humectant, e.g. glycerol. In related embodiments, the citrus honey is replaced with orange blossom honey. Reference to citrus honey and orange blossom honey may be interchangeable herein.

*Citrus* honey, e.g. orange blossom honey, is typically produced by putting beehives in citrus groves during the blooming period. This honey is often made in Florida, Southern California, Texas, France, Italy, Mexico, Spain and Israel, but it can also be made elsewhere in the world. Orange blossom honey can be light to medium in color. Orange blossom honey can contain a number of compounds, such as at least one of quercetin, hesperetin, luteolin, kaempferol, galangin, naringenin and isorhamnetin. The honey can also include various minerals/trace elements, such as zinc, boron, manganese, magnesium, calcium, selenium, copper, potassium and sodium; however, their levels can vary greatly depending on the geographical location from where the honey was produced. Various types of suitable *Citrus* trees are detailed below. The citrus honey may be derived from nectar collected by bees from one or more of these trees.

Suitable types of citrus, e.g. orange blossom, honey include food grade honey. Such honey is available from a number of different suppliers, including HoneyTree Inc. of Onsted, Mich.; Dutch Gold Honey, Inc. of Lancaster, Pa.; and Pure Sweet Honey Farm Inc. of Verona, Wisconsin.

The term "orange" typically applies to the sweet orange—*Citrus sinensis* (L.) Osbeck; however, for purposes of this disclosure, the orange blossom may also be obtained from different orange trees, either in addition, or alternate, to *Citrus sinensis*. *Citrus sinensis* is generally subdivided into four classes with distinct characteristics: common oranges, blood or pigmented oranges, navel oranges, and acidless oranges. Other citrus groups also known as oranges are: Bitter orange (*Citrus aurantium*); Bergamot orange (*Citrus bergamia* Risso); Trifoliate orange (*Poncirus trifoliata*); and Mandarin orange (*Citrus reticulata*).

Common *Citrus* species generally include: *Citrus maxima*—Pomelo; *Citrus medica*—Citron; *Citrus micrantha*—Papeda; and *Citrus reticulata*—Mandarin orange. Important hybrids: *Citrus×aurantiifolia*—Key lime; *Citrus×aurantium*—Bitter orange; *Citrus×latifolia*—Persian lime; *Citrus×limon*—Lemon; *Citrus×limonia*—Rangpur; *Citrus×paradisi*—Grapefruit; *Citrus×sinensis*—Sweet orange; and *Citrus×tangerina*—Tangerine.

Common oranges may also be referred to as "white," "round," or "blond" oranges. Other varieties of common oranges include: Belladonna; Berna; Biondo Comune; Biondo Riccio; Cadanera; Calabrese or Calabrese Ovale; Carvalhal; Castellana; Cherry Orange; Clanor; Dom João; Fukuhara; Gardner; Hamlin; Homosassa; Jaffa orange; Jincheng; Joppa; Khettmali; Kona; Lue Gim Gong; Macetera; Malta; Maltaise Blonde; Maltaise Ovale; Marrs; Midsweet; Moro Tarocco; Mosambi; Narinja; Parson Brown; Pera; Pera Coroa; Pera Natal; Pera Rio; Pineapple; Premier; Rhode Red; Roble; Queen; Salustiana; Sathgudi; Seleta, Selecta; Shamouti Masry; Sunstar; Tomango; Valencia; Verna; Vicieda; and Westin. Oranges different from those considered to be common generally include: Navel oranges; Blood oranges; Acidless oranges; and Xã Đ oái oranges.

The genus *Citrus* has been suggested to originate in Southeast Asia. Prior to human cultivation, it consisted of just a few species, namely: i) *Citrus×aurantiifolia*—Key lime, Omani Lime; *Citrus crenatifolia; Citrus mangshanensis; Citrus maxima*—Pomelo (pummelo, shaddock); *Citrus medica*—Citron; *Citrus reticulata*—Mandarin orange; and *Citrus trifoliata*—Trifoliate orange; ii) Australian limes, including: *Citrus australasica*—Finger Lime; *Citrus australis*—Round lime; *Citrus glauca*—Desert Lime; *Citrus garrawayae*—Mount White Lime; *Citrus gracilis*—Kakadu Lime or Humpty Doo Lime; *Citrus inodora*—Russel River Lime; *Citrus warburgiana*—New Guinea Wild Lime; and *Citrus wintersii*—Brown River Finger Lime; iii) *Citrus japonica*—Kumquats; and iv) Papedas, including: *Citrus halimii*—limau kadangsa, limau kedut kera; *Citrus indica*—Indian wild orange; *Citrus macroptera*; and "Khasi Papeda"—*Citrus latipes*. Various hybrids and cultivars are described below. As each hybrid is the product of (at least) two parent species, they are listed multiple times.

*Citrus maxima*-based types generally include: Amanatsu, natsumikan—*Citrus×natsudaidai* (*C. maxima*×unknown); Cam sánh—(*C. reticulata*×*C.×sinensis*); Grapefruit—*Citrus×paradisi* (*C. maxima*× *C.×sinensis*); Imperial lemon—(*C.×limon*×*C.×paradisi*); Kinnow—(*C.×nobilis*×*C.×deliciosa*); Kiyomi—(*C.×sinensis*×*C.×unshiu*); Lemon—(e.g. *C. maxima*×*C. medica*); Minneola tangelo—(*C. reticulata*×*C.×paradisi*); Orangelo, Chironja—(*C.×paradisi*×*C.×sinensis*); Oroblanco, Sweetie—(*C. maxima*×*C.×paradisi*); Sweet orange—*Citrus×sinensis* (e.g. *C. maxima*×*C. reticulata*); Tangelo—*Citrus×tangelo* (*C. reticulata*×*C. maxima* or *C.×paradisi*); Tangor—*Citrus×nobilis* (*C. reticulata*×*C.×sinensis*); and Ugli—(*C. reticulata*×*C. maxima* or *C.×paradisi*).

*Citrus medica*-based types generally include: Buddha's hand—*Citrus medica* var. *sarcodactylus*; Diamante citron, Florentine citron, Greek citron and Balady citron; Corsican citron and Moroccan citron; Etrog; Fernandina—*Citrus×limonimedica* (e.g. (*C. medica*×*C. maxima*)×*C. medica*); Ponderosa lemon—(e.g. (*C. medica*×*C. maxima*)×*C. medica*); Lemon (e.g. *C. medica*×*C. maxima*); Lumia (e.g. *C. medica*×*C. limon*); Rhobs el Arsa; and Yemenite citron.

*Citrus reticulata*-based types generally include: Bergamot orange—*Citrus×aurantium* ssp. bergamia or *Citrus×bergamia*; Bitter orange, Seville Orange—*Citrus×aurantium*; Blood orange—*Citrus×sinensis* cultivars; Calamondin, Calamansi—(*Citrus reticulata*×*Citrus japonica*); Cam sanh—(*C. reticulata*×*C.×sinensis*); Chinotto—*Citrus×aurantium* var. *myrtifolia* or *Citrus×myrtifolia*; ChungGyun—*Citrus reticulata* cultivar; Clementine—*Citrus×clementina*; Cleopatra Mandarin—*Citrus×reshni*; Siranui—*Citrus reticulata* cv. 'Dekopon' (ChungGyun×Ponkan); Daidai—*Citrus×aurantium* var. *daidai* or *Citrus×daidai*; Grapefruit—*Citrus×paradisi* (*C. maxima*×*C.×sinensis*); Hermandina—*Citrus reticulata* cv. 'Hermandina'; Imperial lemon—((*C. maxima*×*C. medica*)×*C.×paradisi*); Kinnow, Wilking—(*C.×nobilis*×*C.×deliciosa*); Kiyomi—(*C. sinensis*×*C.×unshiu*); Laraha—"*C.×aurantium* ssp. *Currassuviencis*; Mediterranean mandarin, Willow Leaf—*Citrus×deliciosa*; Meyer lemon, Valley Lemon—*Citrus×meyeri* ((*C. maxima*× *C. medica*)×*C.×paradisi* or *C.×sinensis*); Michal mandarin—*Citrus reticulata* cv. 'Michal'; Mikan, Satsuma—*Citrus×unshiu*; Naartjie—(*C. reticulata*×*C. nobilis*); Nova mandarin, Clemenvilla; Orangelo, Chironja—(*C.×paradisi*× *C.×sinensis*); Oroblanco, Sweetie—(*C. maxima*×*C.×paradisi*); Ponkan—*Citrus reticulata* cv. 'Ponkan'; Rangpur, Lemanderin, Mandarin Lime—*Citrus×limonia* ((*C. reticulata*×*C. maxima*)×*C. medica*); Sweet orange—*Citrus×sinensis* (e.g. *C. maxima*×*C. reticulata*); Tangelo—*Citrus×tangelo* (*C. reticulata*×*C. maxima* or *C.×paradisi*); Tangerine—*Citrus×tangerina; Tangor*—*Citrus×nobilis* (*C. reticulata*×*C.×sinensis*); Ugli—(*C. reticulata*×*C. maxima* or *C.×paradisi*); and Yuzu—*Citrus×junos* (*C. reticulata*×*C.×ichangensis*).

Other *Citrus* types generally include: Alemow, Colo—*Citrus×macrophylla*; Djeruk limau—*Citrus×amblycarpa*; Gajanimma, Carabao Lime—*Citrus×pennivesiculata*; Hyuganatsu, Hyuganatsu pumelo—*Citrus tamurana*; Ichang lemon, Ichang Papeda—*Citrus×ichangensis*; Imperial lemon—(*C.×limon*×*C.×paradisi*); Iyokan, anadomikan—*Citrus×iyo*; Kabosu—*Citrus×sphaerocarpa*; Kaffir lime, makrut—*Citrus×hystrix*; Limetta, Sweet Lemon, Sweet Lime, mosambi—*Citrus×limetta*; Palestine sweet lime—*Citrus×limettioides* Tanaka; Odichukuthi—*Citrus Odichukuthi* from Malayalam; Ougonkan—*Citrus flaviculpus* hort ex.Tanaka; Persian lime, Tahiti Lime—*Citrus×latifolia*; Pompia—*Citrus monstruosa, a nomen nudum*; Rough lemon—*Citrus×jambhiri* Lush.; Sakurajima komikan orange; Shekwasha, Hirami Lemon, Taiwan Tangerine—*Citrus×depressa*; Shonan gold—(Ougonkan) *Citrus flaviculpus* hort ex. Tanaka×(Imamura unshiu), *Citrus unshiu* Marc; Sudachi—*Citrus×sudachi*; Sunki, Suenkat—*Citrus×*

*sunki*; Tachibana orange—*Citrus*×*tachibana* (Mak.) Tanaka; and Volkamer lemon—*Citrus*×*volkameriana*.

True *Citrus* species generally include: Citron; Indian wild orange; Kumquat; Mandarin; Mangshanyegan; Papeda; Pomelo; Clymenia; and Australian and Papuan wild limes. Major *Citrus* hybrids include: Grapefruit; Lemon; Lime; and Orange. True and hybrid cultivars generally include: Alemow; Amanatsu; Bergamot orange; Bizzaria; Bitter orange; Blood lime; Blood orange; Buddha's hand; Cam sánh; Cara cara navel; Cherry orange; Citrange; Citrumelo; Clementine; Daidai; Dekopon; Fairchild tangerine; Florentine citron; Hassaku orange; Hebesu; Hyuganatsu; Imperial lemon; Iyokan; Jabara; Jaffa orange; Kabbad; Kabosu; Kaffir lime; Kakadu lime; Kalpi; Key lime; Khasi papeda; Kinnow; Kiyomi; Laraha; Lumia; Mandelo; Mandora; Melanesian papeda; Melogold; Meyer lemon; Murcott; Myrtle-leaved orange tree; Ōgonkan; Orangelo/Chironja; Oroblanco; Palestinian sweet lime; Persian lime; Perrine lemon; Pixie mandarin; Ponderosa lemon; Ponkan; Rangpur; Reikou; Rhobs el Arsa; Rough lemon; Sakurajima komikan orange; Sanboken; Satsuma mandarin; Setoka; Shangjuan; Shonan Gold; Sudachi; Sweet lemon; Sweet limetta; Tangelo; Tangerine; Tangor; Ugli fruit; Valencia orange; Variegated pink lemon; Winged lime; Xã Đoái orange; Yuukou mandarin; and Yuzu.

Buckwheat Honey

In various embodiments, the second humectant/honey comprises buckwheat honey. Buckwheat (e.g. *Fagopyrum esculentum*) is a plant cultivated for its grainlike seeds, and is also used as a cover crop. To distinguish it from a related species, *Fagopyrum tataricum* that is also cultivated as a grain in the Himalayas, primarily in Nepal, Bhutan and India, and from the less commonly cultivated *Fagopyrum acutatum*, it is also known as Japanese buckwheat and silverhull buckwheat.

The scientific classification for buckwheat plants is generally as follows—Order: Caryophyllales; Family: Polygonaceae; and Genera: *Fagopyrum*. Hybrids between two or more species of *Fagopyrum* may also be possible. In various embodiments, the buckwheat honey source can be selected from one or more of the *Fagopyrum* species. In many embodiments, the buckwheat honey is derived from *Fagopyrum esculentum* (or *F. esculentum*). In various embodiments, the honey comprises buckwheat honey and a majority of the honey is derived from blossoms of the genus *Fagopyrum*, optionally from blossoms of the species *Fagopyrum esculentum*. In certain embodiments, the second humectant consists essentially of buckwheat honey, optionally consists of buckwheat honey. Other than serving as a humectant in the composition, buckwheat honey mitigates drying effects of the first humectant, e.g. glycerol.

Buckwheat honey is made by bees that collect pollen and nectar from the little pink flowers (or blossoms) of the common buckwheat plant. This honey is often made in Ohio, Minn., Wisconsin, New York, Pennsylvania and Canada, but it can also be made elsewhere in the world. Buckwheat can be coppery yellow to purple in color, but is often considered a "black" or "dark" honey. It is thought that buckwheat honey has a higher concentration of macronutrients, trace elements, and anti-oxidant compounds relative to many other honey types. It is also thought that darker honeys have the highest concentrations of phenolic compounds, in particular, anti-oxidants and flavonoids.

Suitable types of buckwheat honey include food grade honey. Such honey is available from a number of different suppliers, including those described above for the orange blossom honey.

The second humectant, i.e., honey (e.g. orange blossom and/or buckwheat), may be present in the composition in various amounts. In various embodiments, the second humectant is present in an amount of from about 0.001 to about 99.999, optionally of from about 0.01 to about 99.99, optionally of from about 0.1 to about 99.9, optionally of from about 1 to about 99, optionally of from about 5 to about 95, optionally of from about 10 to about 90, optionally of from about 15 to about 85, optionally of from about 20 to about 80, optionally of from about 25 to about 75, optionally of from about 30 to about 70, optionally of from about 35 to about 65, optionally of from about 40 to about 60, optionally of from about 45 to about 55, or optionally about 50, parts by weight, based on 100 parts by weight of the composition. It is contemplated that any and all values or ranges of values between those described above may also be utilized. Such amounts are generally based on the composition including the first humectant, and can be normalized to account for the inclusion of one or more additional components.

The first and second humectants can be in various weight ratios. In various embodiments, the first and second humectants are present in the composition in a weight ratio (first:second) of from about 12,000:1 to about 1:12,000, optionally of from about 10,000:1 to about 1:10,000, optionally of from about 8,000:1 to about 1:8,000, optionally of from about 6,000:1 to about 1:6,000, optionally of from about 5,000:1 to about 1:5,000, optionally of from about 2,500:1 to about 1:2,500, optionally of from about 1,000:1 to about 1:1,000, optionally of from about 500:1 to about 1:500, optionally of from about 250:1 to about 1:250, optionally of from about 100:1 to about 1:100, optionally of from about 50:1 to about 1:50, optionally of from about 25:1 to about 1:25, optionally of from about 20:1 to about 1:20, optionally of from about 15:1 to about 1:15, optionally of from about 10:1 to about 1:10, optionally of from about 5:1 to about 1:5, optionally of from about 4:1 to about 1:4, optionally of from about 3:1 to about 1:3, optionally of from about 2:1 to about 1:2, or optionally of about 1:1. It is contemplated that any and all values or ranges of values between those described above may also be utilized.

Other Honey Types

In certain embodiments, the composition is substantially free of honey different from orange blossom honey and/or buckwheat honey ("other honey type"). By "substantially free," it is meant that in these embodiments, the other honey type is present in an amount no greater than about 5, optionally no greater than about 2.5, optionally no greater than about 1.5, or optionally approaching or equaling 0, parts by weight, based on 100 parts by weight of the composition. In certain embodiments, the composition is completely free of honey different from orange blossom and/or buckwheat honey. Examples of other types of honey include, but are not limited to honey derived from or generally referred to as: acacia; alfalfa; aster; avocado; basswood; beech wood; blueberry; clover; dandelion; eucalyptus, including blue gum, iron bark, jarrah, red gum and yellow box; field; fireweed; heather; leatherwood; macadamia; manuka; meadow foam; neem; pumpkin; rainforest; rata; rewarewa; pine tree; sage; sourwood; tawari; tupelo; wild flower; honey, and combinations thereof.

Without being bound or limited to any particular theory, unlike with at least orange blossom honey and buckwheat honey, it is believed that some of these other honey types, if not most to all of these other honey types; fail to provide an appreciable beneficial effect in connection with the first humectant. In other embodiments, the composition may include one or more of these other honey types, as they may provide a benefit different from mitigating dryness issues of the first humectant. In these embodiments, one or more of the other honey types may be utilized in the amounts described above for the second humectant.

Occlusive Agents

In certain embodiments, the composition is substantially free of an occlusive agent different from the first and second humectants. By "substantially free," it is meant that in these embodiments, the occlusive agent is present in an amount no greater than about 5, optionally no greater than about 2.5, optionally no greater than about 1.5, or optionally approaching or equaling 0, parts by weight, based on 100 parts by weight of the composition. In certain embodiments, the composition is completely free of an occlusive different from the first and second humectants.

While occlusive agents can increase the water content of the skin by slowing the evaporation of water from the surface of the skin, these ingredients are often greasy and are most effective when applied to damp skin. Mineral oil is often used because of its favorable texture, but it is not as effective at preventing evaporation of water as many other occlusives. Lanolin is expensive and potentially irritating. Silicone derivatives (e.g. dimethicone and cyclomethicone) are not greasy but may have a limited moisturizing effect.

A majority of occlusive agents are mainly lipid (oil) based meaning they leave a slightly greasy sheen over the skin, which can block the pores if used on oily and acne-prone skins. They don't increase the moisture levels of the skin but can help prevent water reserves from being drained by external stressors. The most popular occlusive agents are generally petroleum, lanolin, cocoa butter and jojoba oil. Some occlusive agents can also cause skin irritation, leading to rashes, dry skin, and even acne breakouts. In other embodiments, the composition may include one or more occlusive agents different from the first and second humectants, as they may provide a benefit that outweighs potential deficiencies. In these embodiments, the occlusive agent(s) may be utilized in the amounts described above for the first or second humectant.

Optional Components

Optionally, the composition may include one or more additional components such as additives. Suitable additives include those understood in the art, including but not limited to, moisturizers, emollients, emulsifiers, surfactants, oils, extracts, skin protectants, disinfectants, antiseptics, drugs and drug substances, analgesic compounds, antineuralgic compound, anti-oxidants, blood circulation promoters, antidepressant compounds, anti-anxiety compounds, anti-stress compounds, sunscreens, insect repellants, preservatives, exfoliants, fragrances, colors, fillers, solvents, vehicles, carriers, other types of additives known to those of skill in the art, and combinations thereof. Such additives may be utilized alone or in combination. Various optional additives are described in greater detail below. In general, the optional additives may be of any type used in personal care products and cosmetic products.

It is to be appreciated that certain components or additives may be classified under different terms of art and just because a component or additive is classified under such a term does not mean that they are limited to that function. If utilized, the additive or additives may be present in the composition in various amounts.

The composition may include one or more moisturizers in addition to the first and second humectants. Moisturizers may impart or restore moisture to skin. Increasing skin water content may make the skin softer and more pliable. Moisturizers may serve to mimic the action of normal skin secretions in maintaining suppleness in the skin and provide a barrier to evaporation. Skin moisturizers may include two general types: occlusives and humectants. Occlusive moisturizers form a layer on the skin which reduces the rate of evaporation. Humectants are nonocclusive hygroscopic substances which retain water and make the water available to the skin. Humectants may also function by improving the lubricity of the skin. Both occlusive and humectant moisturizers may be suitable for use in the composition of this disclosure. A moisturizer may be comprised of a single moisturizing ingredient or it may be comprised of a plurality of ingredients which may be included to serve diverse purposes such as emollients, emulsifiers, lipids, surfactants, thickeners, and preservatives. Further, a moisturizer may have both occlusive and nonocclusive properties. Water may be among the ingredients included in a moisturizer. Selection of the levels and types of moisturizers incorporated in the composition may be made without adversely affecting the stability of the composition or its in-use characteristics.

A moisturizer may include long chain $C_{12}$-$C_{22}$ fatty acids, liquid water-soluble polyols, glycerin, propylene glycol, sorbitol, polyethylene glycol, ethoxylated/propoxylated ethers of methyl glucose, ethoxylated/propoxylated ethers of lanolin alcohol, lanolin alcohol, coconut fatty acid, tallow fatty acid, nonocclusive liquid water-soluble polyols, aloe vera gel, aloe vera gel condensed, aloe vera gel freeze-dried powder, aloe vera gel oil extract, amino acids, amniotic fluid, avocadin, calcium protein complex, cashew oil, chia oil, chitin, chitosan, chitosan PCA, cholesteric esters, chondroitin sulfate, collagen, collagen amino acids, copper protein complex, dioctyl maleate, dipentaerythritol fatty acid ester, elastin, ethyl panthenol, evening primrose oil, glycereth-12, glycosphingo lipids, hyaluronic acid, hybrid safflower oil, hydrogenated polyisobutene, hydrolyzed collagen, hydrolyzed elastin, hydrolyzed fibronectin, hydrolyzed mucopolysaccharides, hydrolyzed silk, hydrolyzed wheat protein, jojoba esters, keratin amino acids, kiwi fruit extract, lactamide MEA, liposomes, live yeast cell derivative liposome, marina polyaminosaccharide, mineral oil, mink oil ethyl ether, mucopolysaccharides, mucopolysaccharides, palmetto extract, pantethine, paraffin, PEG-4, PEG-6, PEG-8, PEG-12, PEG-100 stearate, perfluoropolymethyl-isopropyl ether, petrolatum, petroleum wax, pistachio oil, placenta extract, plankton extract, polyamino sugar condensate, polybutene, polyglyceryl methacrylate, polypentaerythrityl tetralaurate, PPG-10 butanediol, PPG-20 methyl glucose ether distearate, royal jelly extract, saccharide isomerate, selenium protein complex, serum albumin, sodium hyaluronate dimethylsilanol, sodium lactate methylsilonol, sodium mannuronate methylsilanol, soluble collagen, super oxide dismutase, super oxide dismutase liposome, tissue extract, tocopheryl linoleate, lipophylic moisturizers such as lysolecithin, lecithin, cholesterol, cholesterol esters, sphingolipids, or ceramides, low molecular moisturizer such as serine, glutamine, sorbitol, mannitol, glycerin, sodium pyrrolidonecarboxylate, 1,3-butylene glycol, propylene glycol, lactic acid, or lactic acid salts, high molecular moisturizers such as hyaluronic acid, sodium hyaluronate, elastin, alginic acid, mucopolysaccharides, polyethylene glycol, polyaspartic acid salts, or water soluble chitin, hydrocarbon oils, hydrocarbon waxes, silicones, fatty acid derivatives, cholesterol, cholesterol derivatives, di- and tri-glycerides, vegetable oils, vegetable oil derivatives, liquid nondigestible oils, blends of liquid digestible or nondigestible oils with solid polyol polyesters, acetoglyceride esters, alkyl esters, alkenyl esters, lanolin and its derivatives, milk tri-glycerides, wax esters, beeswax derivatives, sterols, phospholipids, or any other moisturizer ingredient An occlusive moisturizer may be petrolatum, paraffin, waxes, greases, mineral oil, beeswax, lanolin and oil-soluble lanolin derivatives, saturated and unsaturated fatty alcohols such as behenyl alcohol, squalene, various animal and vegetable oils such as almond oil, apricot oil, apricot pit oil, avocado oil, cade oil, castor oil, cinnamon oil, corn oil, cottonseed oil, evening primrose oil, grape oil, grape seed oil, hazelnut oil, jojoba oil, linseed oil, liver oil, macadamia nut oil, mink oil, neetsfoot oil, olive oil, palm kernel oil, palm nut oil, palm oil, peach pit oil, peanut oil, pine oil, pistachio nut oil, poppyseed oil, rapeseed oil, rice bran oil, rice germ oil, safflower oil, sasanqua oil, sesame oil, sesame seed oil, soybean oil, sunflower oil, sunflower seed oil, tsubaki oil, walnut oil, wheat germ oil, wheat germ oil, teaseed oil, triglycerine, glycerine trioctanate, glycerine triisopalmitate, cacao fat, beef tallow, sheep fat, hog fat, horse fat, hydrogenated oil, hydrogenated castor oil, Japanese wax, shea butter, beeswax, candelilla wax, cotton wax, carnauba wax, bayberry wax, tree wax, spermaceti, montan wax, bran wax, lanolin, reduced lanolin, hard lanolin, kapok wax, sugarcane wax, jojoba wax, shellac wax, or any other moisturizer exhibiting occlusive properties A moisturizer may include agents that mimic natural ingredients and function as botanicals, including vitamins, hydroxy acids, and retinoids. Vitamins may include vitamin A, retinol, retinol palmitate, inositol, pyridoxine chlorate, benzyl nicotinate, nicotinamide, dlα-tocopheryl nicotine, magnesium ascorbyl phosphate, vitamin $D_2$ (ergocalciferol), dlα-tocopherol, potassium dl-α-tocopherol-2-L-ascorbic diester, dl-α-tocopheryl acetate, pantothenic acid, biotin, or any other vitamin. Some ingredients that may reduce the severity of dry skin are alpha hydroxy acids (AHA) and beta hydroxy acids (BHA), including their salts, as well as retinoids. The hydroxy acids are classified according to the number of carboxylic acids on their configuration. Monocarboxylic acids are glycolic, lactic, and mandelic acids. Dicarboxylic acids include malic and tartaric acids. Tricarboxylic acids embody citric acid found in citrus fruits. The BHAs encompass mostly salicylic acid and its derivatives. AHAs have been shown to exfoliate. Thus, they are useful in hyperkeratotic conditions. They act as humectants and have a normalizing effect on the stratum corneum, increasing its plasticity and flexibility. Other ingredients of a moisturizer may include elastin, lecithin, sodium hyaluronate, sodium passive cutaneous anaphylaxis, ceramides, naturally occurring skin lipids and sterols, artificial or natural oils, humectants, emollients, emulsifiers, preservatives, lubricants, greases, natural moisturizing factors (NMF) including low molecular weight substances such as ammonia, amino acids, glucosamine, creatinine, citrate and ionic solutions such as sodium, potassium, chloride, phosphate, calcium and magnesium, sodium pyrrolidone carboxylic acid, hexadecyl, myristyl, isodecyl, or isopropyl esters of adipic, lactic, oleic, stearic, isostearic, myristic and linoleic acids, and their corresponding alcohol esters, sodium isostearoyl-2-lactylate and sodium capryl lactylate, glycerin, polyethylene glycol, propylene glycol, sorbitol, polyethylene glycol and propylene glycol ethers of methyl glucose, polyethylene glycol and propylene glycol ethers of lanolin alcohol, lactic acid, L-proline, and other free fatty acids, coconut fatty acid, tallow fatty acid, nonocclusive liquid water-soluble polyols and the essential amino acid compounds found naturally in the skin, and stearic and lauric acids.

The composition may include one or more emollients in addition to the first and second humectants. Emollients may smooth roughened skin, change the skin's appearance, lubricate, replace natural skin lipids, and provide occlusion. Emollients may be composed of water-in-oil emulsions. An emollient may make something soft or supple, and may also sooth the skin or mucous membrane. Emollients, such as lanolin, shea butter, or petrolatum may act as a barrier (occlusion effect) against loss of water and also as a softener of stratum corneum. Other emollients may be oil-water emulsions of varying composition and may include several esters and oils such as octyl dodecanol, hexyl decanol, oleyl alcohol, decyl oleate, isopropyl stearate, isopropyl palmitate, isopropyl myristate, hexyl laureate, and dioctyl cyclohexane. Further, emollients may include long-chain acylglutamic acid cholesteryl esters, cholesteryl hydroxystearate, 12-hydroxystearic acid, stearic acid, rhodinic acid, lanolin fatty acid cholesteryl ester, petrolatum, cocoa butter, esters of fatty acids, glycerin mono-, di-, and tri-esters, epidermal and sebaceous hydrocarbons such as cholesterol, cholesterol esters, squalane, silicone oils and gums, mineral oil, lanolin and derivatives, castor oil, almond oil, oleyl oleate, or any other emollient ingredient.

The composition may include one or more emulsifiers in addition to the first and second humectants. An emulsifier may be a substance that is capable of lowering the interfacial tension between an oil and an aqueous phase and, thus, may aid the dispersal of oil (in the case of oil-in-water emulsions) and water (in the case of water-in-oil emulsions), respectively, into droplets of a small size and help to maintain the particles in a dispersed state. Emulsifiers may be generally classified as i) proteins or carbohydrate polymers, which act by coating the surface of the dispersed fat or oil particles, thus preventing them from coalescing; such emulsifiers are sometimes also called protective colloids, and ii) long-chain alcohols and fatty acids, which are able to reduce the surface tension at the interface of the suspended particles because of the solubility properties of their molecules. Soaps behave in this manner when they exert cleaning action by emulsifying the oily components of soils.

The composition may include one or more surfactants in addition to the first and second humectants. Surfactants may be detergent, soap base, sodium laurate, sodium palmitate, or any other fatty acid soap, sodium laurosulfate, potassium laurosulfate, or any other higher alkyl sulfate ester salt, POE laurosulfate triethanol amine, sodium POE laurosulfate, or any other alkyl ester sulfate ester salt, sodium lauroylsarcosine or any other N-acylsarcosine acid, sodium N-myristyl-N-methyltaurine, sodium N-cocoyl-N-methyl taurate, sodium laurylmethyl taurate, or any other higher fatty acid amide sulfonate, sodium POE oleyl ether phosphate, POE stearyl ether phosphate, or any other phosphate ester salt, sodium di-2-ethylhexyl-sulfosuccinate, sodium monolauroylmonoethanol amide polyoxyethylene sulfosuccinate, sodium laurylpoly-propylene glycol sulfosuccinate, or any other sulfosuccinate, linear sodium dedecylbenzensulfonate, linear dodecylbenzensulfonate triethanol amine, linear dodecyl benzensulfate, or any other alkylbenzensulfonate, sodium N-lauroylglutamate, disodium N-stearoylglutamate, monosodium N-myristoyl-L-glutamate, or any other N-acylglutamate, sodium hydrogenated castor oil fatty acid glycine sulfate or any other higher fatty acid ester sulfate ester salt, Turkey red oil or any other sulfated oil, POE alkyl ether carboxylic acid, POE alkylaryl ether carboxylate, α-olefinsulfates, higher fatty acid ester sulfonates, secondary alcohol sulfate ester salts, higher fatty acid alkylolamide sulfate ester salts, sodium lauroyl monoethanolamide succinate, N-palmitoyl asparaginate ditriethanol amine, sodium caseine, or any other anionic surfactant, stearyl trimethyl ammonium chloride, lauryl trimethyl ammonium chloride, or any other alkyl trimethyl ammonium salt, distearyldimethyl ammonium chloride, dialkyldimethyl ammonium chloride salts, poly(N,N'-dimethyl-3,5-methylenepiperidinium)chloride, cetylpyridinium chloride or any other alkyl pyridinium salt, alkyl quaternary ammonium salts, alkyl dimethylbenzyl ammonium salts, alkyl isoquinolinium salts, dialkyl morphonium salts, POE alkyl amines, alkyl amine salts, polyamine fatty acid derivatives, amyl alcohol fatty acid derivatives, benzalkonium chloride, benzethonium chloride, or any other cationic surfactant, sodium 2-undecyl-N,N,N-(hydroxyethylcarboxymethyl)-2-imidazoline, 2-cocoyl-2-imidazoliniumhydroxide-1-carboxyethyloxy-2-sodium salt, or any other imidazoline family bipolar surfactant, 2-heptadecyl-N-carboxymethyl-N-hydroxyethylimidazolinium betaine, lauryldimethyl-aminoacetate betaine, alkyl betaine, amide betaine, sulfo betaine, or any other betaine family surfactant, or any other bipolar surfactant, sorbitan monooleate, sorbitan monoisostearate, sorbitan monolaurate, sorbitan monopalmitate, sorbitan monostearate, sorbitan sesquioleate, sorbitan trioleate, diglyceryl sorbitan pentaoctanoate, diglyceryl sorbitan tetraoctanoate, or any other sorbitan fatty acid ester, glycerin mono cotton seed oil fatty acid, glycerin monoerucate, glycerin sesquioleate, glycerin monostearate, glycerin α,α-oleate pyroglutamate, monostearate glycerin malic acid or any other glycerin or polyglycerin fatty acid, propylene glycol monostearate or any other propylene glycol fatty acid ester, hydrogenated castor oil derivatives, glycerin alkyl ethers, polyoxyethylene methylpolysiloxane copolymers, or any other lyophilic nonionic surfactant, POE sorbitan monooleate, PO-sorbitan monostearate, POE-sorbitan monooleate, POE-sorbitan tetraoleate, or any other POE sorbitan fatty acid ester, POE-sorbite monolaurate, POE-sorbitan monooleate, POE-sorbite pentaoleate, POE-sorbitan monostearate, or any other POE sorbitan fatty acid ester, POE-glycerin monostearate, POE-glycerin monoisostearate, POE-glycerin triisostearate, or any other POE glycerin fatty acid ester, POE monooleate, POE distearate, POE monodioleate, distearate ethylene glycol, or any other POE fatty acid ester, POE lauryl ethers, POE oleyl ethers, POE stearyl ethers, POE behenyl ethers, POE2-octyldodecyl ethers, POE cholestanol ethers, or any other POE alkyl ether, POE octyl phenyl ethers, POE nonyl phenyl ethers, POE dinonyl phenyl ethers, or any other POE alkyl phenyl ether, Pluronic or any other poloxamer, POE.POP cetyl ethers, POE.POP-2-decyltetradecyl ethers, POE.POP monobutyl ethers, POE.POP hydrated lanolin, POE.POP glycerin ethers, or any other POE-POP alkyl ether, Tetronic or any other tetra-POE.tetra-POP ethylene diamine condensation product, POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleic acid or any other POE castor oil hydrogenated castor oil derivative, POE sorbitan beeswax or any other POE beeswax lanolin derivative, coconut oil fatty acid diethanolamide, laurate monoethanolamide, fatty acid isopropanolamide, or any other alkanolamide, POE propylene glycol fatty acid esters, POE alkylamines, POE fatty acid amides, sucrose fatty acid esters, POE nonylphenyl formaldehyde condensation products, alkylethoxydimethylamineoxide, trioleylphosphoric acid, or any other hydrophilic nonionic surfactant, or any other surfactant.

The composition may include one or more oils in addition to the first and second humectants. Oils may act as penetrating transdermal carriers that penetrate the skin the quickly and aid in transport of other components present in the composition of the present invention. Examples of oils that may be utilized include almond oil, anise oil, apricot kernel oil, apricot oil, avocado oil, balm mint oil, basil oil, bee balm oil, bergamot, bergamot oil, birch oil, bitter almond oil, bitter orange oil, caraway oil, cardamom oil, castor oil, cedarwood oil, cinnamon oil, clay oil, clove oil, cloveleaf oil, coconut oil, fractionated coconut oil, cottonseed oil, cypress oil, eucalyptus oil, evening primrose oil, fennel oil, gardenia oil, geranium oil, ginger oil, grapefruit oil, grape seed oil, hazelnut oil, hops oil, hyptis oil, indigo bush oil, jasmine oil, jojoba oil, juniper oil, kiwi oil, kukui nut oil, laurel oil, lavender oil, lemon oil, lemongrass oil, linden oil, linseed oil, lovage oil, macadamia nut oil, maize oil, *matricaria* oil, musk rose oil, neroli oil, nutmeg oil, olibanum, olive oil, orange flower oil, orange oil, palm oil, patchouli oil, peach kernel oil, peanut oil, pecan oil, pennyroyal oil, peppermint oil, persic oil, pine oil, pine tar oil, poppy-seed oil, pumpkin seed oil, rapeseed oil, rose oil, rose hips oil, rosemary oil, rue oil, sage oil, sambucus oil, sandalwood oil, sassafras oil, sesame oil, silver fir oil, soybean oil, spearmint oil, sunflower oil, sweet almond oil, sweet marjoram oil, sweet violet oil, tar oil, tea tree oil, thyme oil, wheat germ oil, wild mint oil, yarrow oil, ylang ylang oil, walnut oil, tall oil, thistle seed oil, hydrogenated vegetable oils, or any other suitable oil.

The composition may include one or more extracts in addition to the first and second humectants. Examples of extracts that may be utilized include acacia extract, alfalfa extract, algae extract, aloe extract, aloe vera gel, aloe vera gel condensed, althea extract, anise extract, apple extract, apricot extract, apricot kernel oil, arnica extract, artichoke extract, asafoetida extract, avocado extract, azulene, balm mint extract, balm mint oil, banana extract, barley extract, bee pollen extract, bioflavonoids, birch leaf extract, black cohosh, black currant extract, black walnut extract, bladderwrack extract, borage extract, botanical extracts, burdock extract, burnet extract, butcher's broom extract, calendula extract, camomile extract, caper extract, carrageenan extract, carrot extract, carrot oil, centella, cherry bark extract, *cinchona* extract, cinquefoil extract, citroflavonoid water soluble, citrus bioflavonoid complex, clover blossom extract, coltsfoot extract, cornfrey extract, coneflower extract, cornflower extract, corn silk extract, couch grass, crataegus extract, cucumber extract, cypress extract, dandelion extract, elder flower extract, eleuterococcus, elm bark extract, licorice extract, eucalyptus extract, everlasting extract, fennel extract, fenugreek extract, fern extract, gardenia extract, garlic extract, gerrtian extract, gingko biloba extract, ginko extract, ginseng extract, glycyrrhetinic acid, glycyrrhizic acid, grape extract, grape leaf extract, grape skin extract, guarana extract, Hawaiian ginger extract, hayflower extract, helichrysum, henna extract, hesperidin complexes, hesperidin methyl chalcone, *hibiscus* extract, hops extract, horse chestnut extract, horsetail extract, *hypericum* extract, indian cress extract, ivy extract, juniper extract, kelp extract, kiwi extract, *laminaria* extract, lavender extract, lemon balm, lemon extract, lettuce extract, licorice extract, linden extract, madder, mallow extract, *matricaria* extract English, milfoil extract, mistletoe extract, mushroom extract, myrrh extract, nettle extract, oak root extract, oat extract, onion extract orange blossom extract, orange flowers extract, pansy extract, parsley extract, pellitory extract, pennyroyal extract, peppermint extract, periwinkle extract, pine needle extract, plantain extract, pollen extract, quince seed, rauwolfia extract, restharrow extract, rhatany extract, rhubarb root extract, rice bran extract, rose hips extract, rosemary extract, sage extract, sambucus extract, sanguinaria root extract, saponaria extract, sea weed extract, soy extract, soy protein, soy sterol, spearmint extract, sulfur tar complex, sunflower extract, sweet clover extract, tea extract, tea tree oil, thistle extract, thyme extract, tomato extract, tormentill extract, valerian extract, walnut extract, water cress extract, wheat bran extract, wheat germ extract, white nettle extract, white willow bark extract, wild indigo, witch hazel extract, yarrow extract, zedoary oil, ginger oil, cinnamon oil, sugar cane extract, citrus blossom extract, pineapple extract, licorice oil, olive oil, carrot seed oil, jojoba oil, wheat germ, aloe barbadensis extract, apricot extract, arnica montana extract, balm mint extract, bamboo extract, bearberry extract, beet extract, bilberry extract, birch leaf extract, blackberry leaf extract, bladderwrack extract, buckwheat extract, burdock extract, butcherbroom extract, calendula extract, carrot extract, *matricaria* extract, cherimoya extract, jujube extract, coltsfoot extract, comfrey extract, coneflower extract balsam copaiba, cornflower extract, cucumber extract, dog rose hips extract, fennel extract ginger extract, ginkgo extract, ginseng extract, *camellia sinensis* extract, guarana extract, *crataegus monogina* extract, hayflower extract, henna extract, hops extract, horsetail extract, horsechestnut extract, hydrocotyl extract, ivy extract, Job's tears extract, *juniperus communis* extract, Karite extract, kiwi extract, lady's mantle extract, *laminaria digitata* extract, lavender extract, lemon peel extract, licorice extract, linden extract, *lithospermum officinale* extract, mallow extract, mango extract, marshmallow extract, melon extract, mimosa tenuiflora bark extract, white oak bark extract, English oak extract, oyster shell extract, pansy extract, peach extract, *capsicum frutescens* oleoresin, *capsicum frutescens* extract, peppermint extract, *quillaja saponaria* extract, raspberry extract, *krameria triandra* extract, rosemary extract, sage extract, St. John's wort extract, stinging nettle extract, strawberry extract, soapwort extract, thyme extract, walnut extract, watercress extract, wheat germ extract, willow bark extract, witch hazel extract, or any other extract.

The composition may include one or more skin protectants in addition to the first and second humectants. Examples of suitable skin protectants that may be utilized include allantoin, aloe vera gel, anise extract, avocado oil unsaponifiables, carboxymethyl chitin, chondroitin sulfate, collagen, collagen amino acids, embryo extract, glyceryl ricinoleate, hydrolyzed animal elastin, hydrolyzed milk protein, hydrolyzed vegetable protein, linoleic acid (and) linolenic acid (and) arachidonic acid, liposomes, perfluoropolymethyl-isopropyl ether, plankton extract, and spine marrow extract.

The composition may include one or more disinfectants, antiseptics, and/or drug substances, in addition to the first and second humectants. Incorporation of one or more disinfectants or antiseptics is especially useful in those situations where it is important to inactivate the microorganisms which remain on the skin after normal cleansing. Incorporation of a drug substance in the composition may be useful for the prevention or treatment of various skin disorders or to deliver drug substances to the skin which are advantageously administered topically for percutaneous absorption.

Examples of suitable disinfectants and antiseptics that may be utilized include ambazone, benzoic acid, bithionol, bromsalans, dibromsalan, metabromsalan, tribromsalan, camphor, carbolic acid, cethexonium bromide, chlorhexidine acetate, chlorhexidine gluconate solution, chloroazodin, chlorocresol, chlorothymol, chloroxylenol, clorophene, cresol, dichlordimethylhydantoin, dichlorobenzyl alcohol, dichloroxylenol, dofamium chloride, domiphen bromide, ethacridine lactate, menthol, methylbenzethonium chloride, nitromersol, noxythiolin, and triclosan. Other relevant examples are sodium pyrithione, sodium ricinoleate, thimerosal, trichlocarban, undecylenamidopropyltrimethyl ammonium methosulfate, undecylenic acid, zinc pyrithione, and zinc undecylenate, or any other disinfectant or antiseptic A drug substance may be any compound or mixture thereof that may produce a beneficial effect on the human to whom the drug substance has been given. Drug substances may be any physiologically or pharmacologically substance that produces a localized or systemic effect in mammals including humans. Examples of suitable drug substances that may be utilized include anti-inflammatory compounds, analgesics, tranquilizers, cardiac glycosides, narcotic antagonists, antiparkinsonism agents, antidepressants, antineoplastic agents, immunosuppressants, antiviral agents, antibiotic agents, appetite suppressants, antiemitics, antihistamines, antimigraine agents, coronary, cerebral or peripheral vasodilators, antianginals, calcium channel blockers, hormonal agents, contraceptive agents, antithrombotic agents, antihypertensive agents, chemical dependency drugs, local anesthetics, corticosteroids, dermatological agents and the like, vitamins like vitamin A such as all-trans retinol, retinol acetate, retinol palmitate, retinol propionate, betacarotene, halibut-liver oil, shark-liver oil, vitamin $B_1$ such as thiamine hydrochloride, benfotiamine, bisbentiamine, bisbutiamine, bisibutiamine, betoiamine hydrochloride, cetotiamine hydrochloride, cocarboxylase, cycotiamine, fursultiamine, vitamin $B_2$ such as riboflavine, riboflavine tetrabutyrate, flavine adenine dinucleotide, vitamin $B_6$, vitamin $B_{12}$ such as cobalamins, $B_{12}$ TAM, cobamamide, cyanocobalamin, mecobalamin, other vitamins of the B group, vitamin C such as ascorbic acid, vitamin D such as ergocalciferol (vitamin $D_2$), cholecalciferol (vitamin $D_3$), calcifediol, calcitriol, alfacalcitriol, dihydrotachysterol, alfacalcidol, calcifediol, calcitriol, cholecalciferol, cod-liver oil, dihydrotachysterol, ergocalciferol, vitamin E, alpha tocopherols, tocopheryl nicotinate, tocopherylquinone, wheat-germ oil, vitamin K such as phytomenadione, menadiol sodium diphosphate, menadione, vitamin P, sucrose sulfate esters such as sucralfate, sucrose octasulfate and salts, esters and complexes thereof, antibacterials such as phenoxyethanol, or any other drug substance.

The composition may include one or more analgesic compounds in addition to the first and second humectants. Examples of suitable analgesic compounds that may be utilized include aloe vera, MSM, emu oil, menthol, glucosamine, chondroitin, a capsaicinoid, arnica extract, coriander oil, Roman chamomile oil, willow bark extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, gingkgo, juniper, lavender oil, licorice, marjoram, meadow sweet, menthol, passion flower, quercetin, salicinum, wild yam, wintergreen, wood betony, wormwood, or any other analgesic.

The composition may include one or more anti-inflammatory compounds in addition to the first and second humectants. Examples of suitable anti-inflammatory compounds that may be utilized include aloe vera, MSM, emu oil, chondroitin, glucosamine, a capsaicinoid, arnica extract, grape seed extract, coriander oil, marigold extract, nettle leaf extract, Roman chamomile oil, blue-bottle extract, St. John's wort, willow bark extract, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, elderflower, evening primrose oil, flaxseed, ginkgo, ginger, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin, shea butter, turmeric, wild yam, wormwood, yucca, bisabolol, sucralfate, LIPACIDE, gauaiazulene, essential fatty acids, polyunsaturated fatty acid derivatives from plant seed oils and other vegetable sources, or any other anti-inflammatory. Essential fatty acids (EFAs) may include omega-3 and omega-6 fatty acids such as linolenic acid and alpha linolenic acid. In addition, any known herbs or various compounds that contain EFAs may be included in the composition. Examples of such herbs include flaxseed and evening primrose oil.

The composition may include one or more antineuralgic compounds in addition to the first and second humectants. Compounds having antineuralgic effects generally provide relief of pain or discomfort along a course of a nerve or in an area of distribution of the nerve. Suitable antineuralgics that may be utilized include a capsaicinoid, Roman chamomile oil, coriander oil, or any other antineuralgic compound.

The composition may include one or more anti-oxidants in addition to the first and second humectants. Compounds having anti-oxidant activity generally prevent damage or deterioration of tissue. Examples of suitable anti-oxidants that may be utilized include chondroitin, ascorbic acid, vitamin C, cocoa butter, grape seed extract, St. John's wort extract, coriander oil, cysteine, barley grass, bilberry, Echinacea, garlic, ginger, ginkgo, ginseng, grape seed proanthocyanidin extract, green tea, Hawthorne, lemon balm, milk thistle, oregano, peppermint, pomegranate juice, purslane, pycnogenol, red wine, rosemary, schizandra, wuweizi, wurenchun, trilinolein, sanchi, tartaric acid, turmeric, α-tocopherol or any other tocopherol, dibutylhydroxytoluene butylhydroxyanisole, or any other anti-oxidant.

The composition may include one or more blood circulation promoters in addition to the first and second humectants. Blood circulation promoters generally provide increased blood circulation to an area to which the composition is applied. Examples of suitable blood circulation promoters that may be utilized include MSM (methylsulfonylmethane), arnica extract, Roman chamomile oil, nettle extract, marigold extract, grape seed extract, blue-bottle extract, coriander oil, lime tree extract, marigold extract, feverfew extract, St. John's wort extract, witch hazel extract, arjuna, Bala, benzoin, bilberry, black pepper, blue gum eucalyptus, blue vervain, borneol, butcher's broom, cayenne, cypress, geranium, ginger, ginkgo, grape seed proanthocyanidin extract, Hawthorne, L-arginine, lemon, lemon grass, linden flowers, niaouli, oat straw, orange blossom, passion flower, Peru balsam, pine, prickly ash bark, rose oils, rosemary, Spanish sage, spruce, Tien Chi ginseng, thyme, violet, white birch, yohimbe, or any other blood circulation promoter.

The composition may include one or more compounds having antidepressant, anti-anxiety, or anti-stress activity in addition to the first and second humectants. Examples of suitable antidepressant, anti-anxiety, or anti-stress compounds that may be utilized include MSM, kava kava extract, Roman chamomile extract, feverfew extract, St. John's wort extract, bee pollen, bergamot, black cohosh, black horehound, bugleweed, California poppy, clary sage, cowslip, damiana, DHEA (dehydroepiandrosterone), geranium, ginseng, gotu kola, grapefruit, hyssop, Jamaican dogwood, lady's slipper, lavender, lemon balm, licorice, linden, lobelia, mate, mistletoe, motherwort, mugwort, oat straw, passion flower, peppermint, rosemary, skullcap, valerian root, vervain, wild lettuce, wood betony, or any other antidepressant, anti-anxiety, or anti-stress compound.

In addition to the first and second humectants, the composition may further include any pain relieving, anti-inflammatory, anti-oxidant, blood circulation promoter, anti-depressant, anti-anxiety, or anti-stress type of herb. Examples of suitable herbs that may be utilized include arjuna, Bala, barley grass, bee pollen, benzoin, bergamot, bilberry, black cohosh, black horehound, black pepper, blue gum eucalyptus, blue vervain, borage, borneol, Boswellia, bromelain, bugleweed, bupleurem, burdock, butcher's broom, California poppy, camphor, cayenne, clary sage, cocash weed, cowslip, coughweed, cypress, damiana, dandelion, devil's claw root, DHEA, echinacea, elderflower, evening primrose oil, flaxseed, garlic, geranium, ginger, ginkgo, ginseng, golden groundsel, golden ragwort, golden Senecio, gotu kola, grapefruit, grape seed proanthocyanidin extract, green tea, grundy swallow, Hawthorne, heather, hyssop, Jamaican dogwood, juniper, kaempferol, L-arginine, lady's slipper, lavender, lemon, lemon balm, lemon grass, licorice, life root, linden, lobelia, marjoram, mate, meadow sweet, milk thistle, mistletoe, motherwort, mugwort, NDGA (nordihydroguaiaretic acid), neem, niaouli, oat straw, orange blossom, oregano, Padma 28, passion flower, peppermint, Peru balsam, pine, pomegranate juice, prickly ash bark, purslane, pycnogenol, quercetin, ragwort, red wine, rose oils, rosemary, salicinum, schizandra, sharp sorrel, skullcap, Spanish sage, spruce, squaw weed, Tien Chi ginseng, thyme, trilinolein, turmeric, valerian root, vervain, violet, white birch, wild lettuce, wild yam, wintergreen, wood betony, wormwood, yohimbe, yucca, or any other pain relieving, anti-inflammatory, anti-oxidant, blood circulation promoting, anti-depressant, anti-anxiety, or anti-stress type of herb.

The composition may include one or more extracts in addition to the first and second humectants. The extracts may have various medicinal effects. Examples of suitable extracts that may be utilized include aloe extract, candock extract, carrot extract, *cinchona* extract, clove extract, common fennel extract, cornflower extract, creeping saxifrage extract, cucumber extract, dishcloth gourd extract, eucalyptus extract, field horsetail extract, hamamelis extract, herbaceous peony extract, horse chestnut extract, *Houttuynia cordate* extract, iris rhizome extract, lemon extract, licorice root extract, *Lithospermum erythrorhizon* extract, melilot extract, melissa extract, mulberry extract, peach extract, peach leaf extract, *Phellon dendron amurense Rupr* extract, placenta extract, primrose extract, raspberry extract, rose extract, *Rehmannia glutinosa* extract, sage extract, seaweed extract, silk extract, soapwort extract, *Sophora angustifolia* extract, tea extract, thyme extract, thymus extract, white dead nettle extract, or any other medicinal extract.

The drug and medicinal ingredients that may be included in the composition are not limited by the above-mentioned ingredients. Drug and medicinal ingredients may be formulated alone into the composition or two or more types of medicinal ingredients may be combined and formulated suitably depending upon the objective. Further, drug and medicinal ingredients may not only be used in a free form, but may also be formulated into the composition in the form of a salt of an acid or base when capable of forming a salt or in the form of an ester when having a carboxylic acid group.

The composition may include one or more sunscreens in addition to the first and second humectants. Examples of suitable sunscreens that may be utilized include allantoin, PABA, p-aminobenzoates, benzophenone-2, benzophenone-6, benzoresorcinol, benzyl salicylate, cinoxate, dioxybenzone, esculoside, ethyl 4-bis(hydroxypropyl)aminobenzoate, ethylhexyl p-methoxycinnamate, etocrylen, glyceryl aminobenzoate, homosalate, methyl salicylate, methyl anthranilate, methyl eugenol, 3-(4-methylbenzylidene)boran-2-one, mexenoe, octabenxone, octocrylene, oxybenzone, padimate, 2-phenyl-1H-benzimidazole-5-sulphonic acid, sulisobenzone, 3-benzylidene camphor, coffee extract, ethyl salicylate, glyceryl PABA, homosalate, isopropylbenzylsalicylate, menthyl anthranilate, nylon-12 (and) titanium dioxide, octyl dimethyl PABA, octyl methoxycinnamate, octyl salicylate, octyl triazone, orizanol, PEG-25 PABA, TEA-salicylate, titanium dioxide, zinc oxide, benzophenone-1, benzophenone-3, benzophenone-4, bensophenone-8, benzophenone-9, benzophenone-11, benzophenone-12, butyl methoxydibenzoylmethane, 4-isopropyl dibenzoyl methane, avocadin, argana oil, DEA-methoxycinnamate, drometrizole, ethyl dihydroxypropyl p-aminobenzoic acid, etocrylene, isopropyl methoxycinnamate, 3-(4-methylbenzylidene)-camphor, octocrylene, octrizole, octyl dimethyl PABA, octyl methoxycinnamate, octyl salicylate, octyl triazone, PABA, shea butter, TEA-salicylate, tri-PABA-panthenol, or any other sunscreen.

The composition may include one or more insect repellants in addition to the first and second humectants. Examples of suitable insect repellents that may be utilized include butopyronoxyl, butylethylpropanediol, dibutyl phthalate, diethyltoluamide, dimethyl phthalate, ethohexadiol, citronella, camphor, or any other insect repellant.

The composition may include one or more preservatives in addition to the first and second humectants. Examples of suitable preservatives that may be utilized include grape seed extract, cocoa butter, methylparaben, propylparaben, diazolindinyl urea, sorbic acid, phenoxyethanol, ethylparaben, butylparaben, sodium butylparaben, caprylyl glycol, dehydroacetic acid, or any other preservative. The composition may or may not include a preservative, and may include a plurality of preservatives. Preservatives may help to prevent bacteria and fungus from developing in the composition. Preservatives may also increase the shelf life of the composition. Shelf life may refer to the time between when the composition is produced and the time the composition is applied to a skin surface. Preservatives may serve different purposes which are known to those having skill in the art.

In addition to the first and second humectants, the composition may further include sugar (e.g. white sugar, brown sugar, etc.), or a sugar equivalent, or other exfoliants or granular materials which assist in exfoliation. Examples of suitable exfoliants that may be utilized include pumus, apricot meal, ground oats, walnut shell flour, and ground almond meal. One embodiment of the composition includes white sugar.

The composition may include one or more fragrances and/or colors (e.g. pigments, dyes, etc.) in addition to the first and second humectants. Any type of natural or synthetic fragrance, such as floral, herbal or fruity fragrance could be utilized. The use of fragrance is well known in the cosmetic art and in the art of over-the-counter drug formulation, and many suitable fragrances are known in the art. The stability and function of the composition is generally not altered by the presence or absence of fragrance. Freesia essential oil may be used as a natural fragrance. Other essential oils may also be used as a natural fragrance. Fragrance can be omitted, and it may be desirable to omit fragrance in circumstances in which the composition is intended for use on sensitive individuals or individuals who may undergo an allergic reaction to fragrance. Any type of natural or FD&C colorant, such as FD&C Blue No. 1, may be utilized. Optionally, the composition may be colorless, or possess a color provided by one or more of the compounds present therein.

In addition to the first and second humectants, the composition may further include various pharmaceutically or cosmetically acceptable excipients or additives such as those which usually are employed in cosmetic or pharmaceutical compositions. Excipients or additives may be pH adjusting agents, stabilizing agents, coloring agents, foaming agents, viscosity adjusting agents, skin lightening agents such as arbutin, fillers or thickening agents such as alginate and Carbomer-940, spreading agents, pearl gloss agents, agents which protect the skin against aggressive substances in water, atmospheric air and on solid surfaces such as salts, pigments, fats, and esters, protecting agents such as chitosan, salts, waxes, and long chain alcohols. Other additives include lactic acid, citric acid, glycolic acid, succinic acid, tartaric acid, dl-malic acid, potassium carbonate, sodium hydrogencarbonate, ammonium hydrogencarbonate, and other pH adjusters. It is to be appreciated that various combinations of the aforementioned additives may be utilized in the composition of this disclosure. In addition, other suitable additives are described in the EXAMPLES section below. Moreover, the composition may be substantially free, or completely free, of such components.

Composition

This disclosure also provides the composition as described above. The composition may be formulated to include a cosmetically acceptable carrier (or vehicle) and prepared and/or packaged and labeled as moisturizing skin, preventing skin dryness, treating skin dryness, etc. The composition may be administered topically. Examples of cosmetically acceptable carriers include, but are limited to, water, glycerin, waxes, various alcohols such as ethanol, propyl alcohol, vegetable oil, mineral oil, silicones such as silicone oils, fatty esters, fatty alcohols, glycols, polyglycols or any combinations thereof. Further examples are described in the optional additives above, as well as in the EXAMPLES section below.

The compositions of this disclosure can be prepared using various methods understood in the art. In one example of preparing the composition, the preparation method comprises the step of combining the first and second humectants, optionally along with one or more additional components (e.g. carriers and/or additives) as described above, to obtain the composition. The components can be combined using conventional manufacturing methods and apparatuses, e.g. a mixer, a blender, etc.

Finished compositions (or products) may be in any form suitable for topical application to the skin such as, but not limited to, aerosol spray, gel, cream, dispersion, emulsion, foam, liquid, lotion, mousse, patch, pomade, powder, pump spray, solid, solution, stick or towelette. Emulsions may include oil-in-water emulsions, water-in-oil emulsions and water-in-silicone emulsions. In various embodiments, the composition may be used in the form of a pharmaceutical, quasi-pharmaceutical, or cosmetic. It may take the form of a lotion, cream, ointment, powder, gel, aerosol, foam, facial cleanser, balm, gel, shampoo, conditioner, wash, rinse, towelette, beauty liquid, pack, mask, makeup, foundation, scrub, exfoliant, soap, lipstick, hair cosmetic, body cosmetic, or any other suitable form for application to external surfaces of the body. The form capable of being taken by the composition is not limited to these forms however. In certain embodiments, the composition is in the form of a topical composition, optionally in the form of a topical lotion, topical wash, topical créme, topical bar, topical stick, or combinations thereof.

Further specific examples of products that comprise (or are) the composition of this disclosure include hand creams, body lotions, body milks (or lotions), complexion bars, body washes, liquid soaps (e.g. dilute or concentrated), bar soaps, deodorants and/or antiperspirants (e.g. roll-on). The first and second humectants may be present in such products in various amounts.

In certain embodiments, the first humectant is present in the product in an amount of from about 0.001 to about 15, optionally of from about 0.01 to about 12.5, optionally of from about 0.1 to about 10, optionally of from about 0.5 to about 9, optionally of from about 0.9 to about 8.5, optionally of from about 1 to about 8, optionally of from about 1.5 to about 7.5, optionally of from about 2 to about 7, optionally of from about 2.5 to about 6.5, optionally of from about 3 to about 6, optionally of from about 4 to about 5, or optionally about 5, wt. %. It is contemplated that any and all values or ranges of values between those described above may also be utilized.

In certain embodiments, the second humectant is present in the product in an amount of from about 0.001 to about 15, optionally of from about 0.01 to about 12.5, optionally of from about 0.1 to about 10, optionally of from about 0.5 to about 9, optionally of from about 0.9 to about 8.5, optionally of from about 1 to about 8, optionally of from about 1.5 to about 7.5, optionally of from about 2 to about 7, optionally of from about 2.5 to about 6.5, optionally of from about 3 to about 6, optionally of from about 4 to about 5, or optionally about 5, wt. %. It is contemplated that any and all values or ranges of values between those described above may also be utilized.

The following examples, illustrating the methods and compositions of this disclosure, are intended to illustrate and not to limit the invention.

EXAMPLES

A series of humectants commonly used or considered for use in skin care products were evaluated for humectancy in both (ambient) 23° C./50-70% Relative Humidity (RH) and 40° C./85% RH. Results indicate that humectancy is primarily active in high RH conditions (see FIG. 1).

These humectant candidates were further evaluated for effects on human skin keratinocytes (HEK001). Flow cytometry (FACSCalibur, Becton Dickinson, N.J.) was utilized to measure cell growth, as indicated by cell size and captured by forward scatter (FSC) mean values normalized to control treatments. This technique measures cell size after an exposure, in vitro, to various chemicals. A range of responses were discovered with some humectants promoting cell growth, some having no effect and some causing a decline in skin cell growth as measured by cell size.

Figure 2:
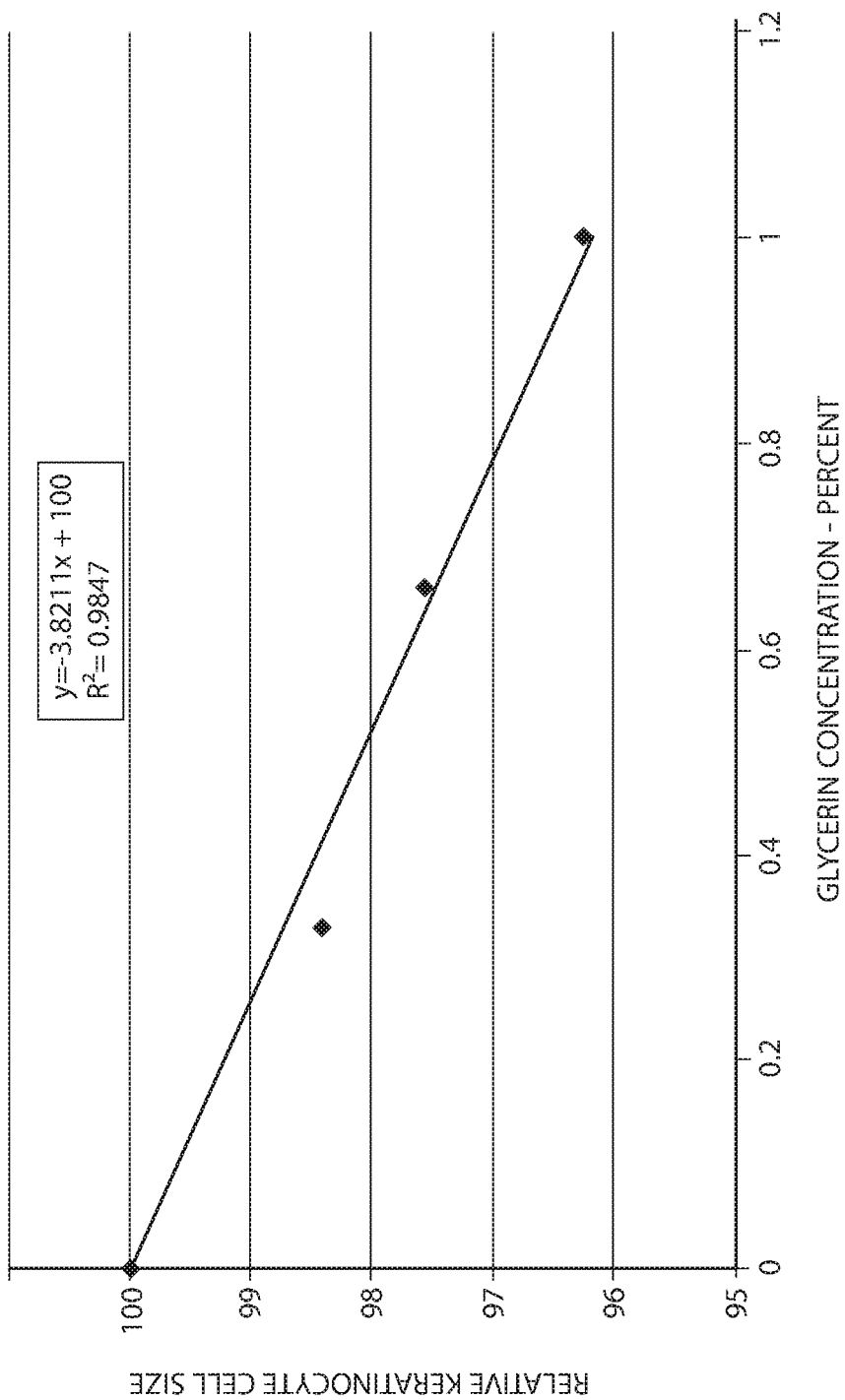
FIG. 2 is a graph illustrating glycerin and keratinocyte cell growth as measured by cell size.

One commonly used skin care humectant, glycerin, was, surprisingly, found to cause a decline in skin cell growth as measured by cell size (see FIG. 2). One honey, manuka, widely promoted for its wound healing benefits was found to cause a decline in skin cell growth as measured by cell size. Whereas two types of honey, buckwheat and orange blossom, were found to increase cell growth as measured by cell size. The honeys used for the examples are food grade honeys.

Figure 3:
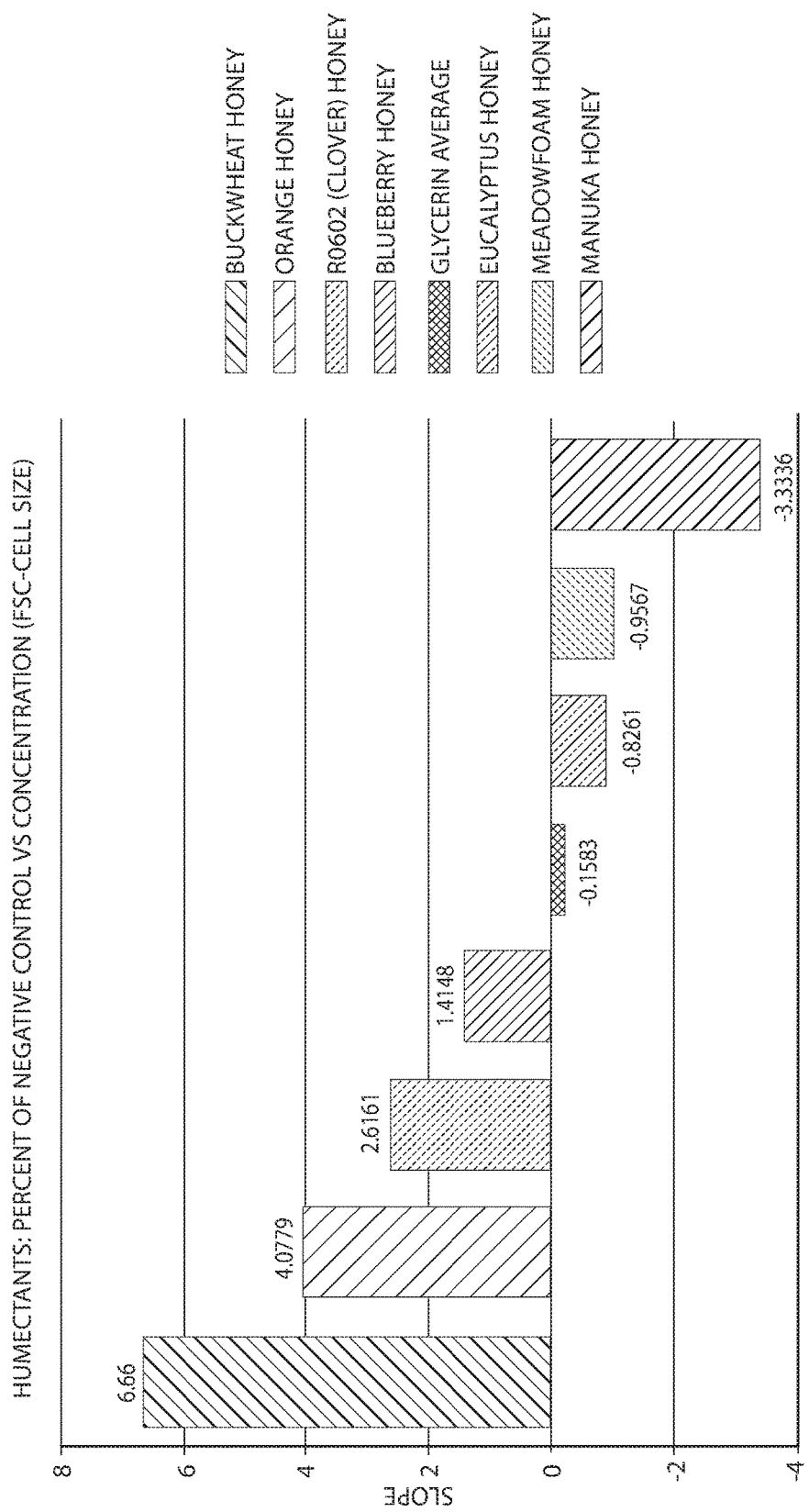
FIG. 3 is a graph illustrating the effect of different types of honey on keratinocyte cell growth as measured by cell size.

As can be seen in FIG. 3, a positive slope of the honey type indicates increasing cell size and a negative slope indicates decreasing cell size. Upon consideration of the data, and without being bound or limited by any particular theory, it is believed that some humectants may be too powerful. Since humectancy is primarily a high RH phenomenon, in winter when the air is dry, the humectant may be drawing moisture from the skin cells and having negative effects on cell growth. It was postulated that certain types of honey, including buckwheat and orange blossom, might be able to mitigate the negative effects of glycerin.

Figure 4:
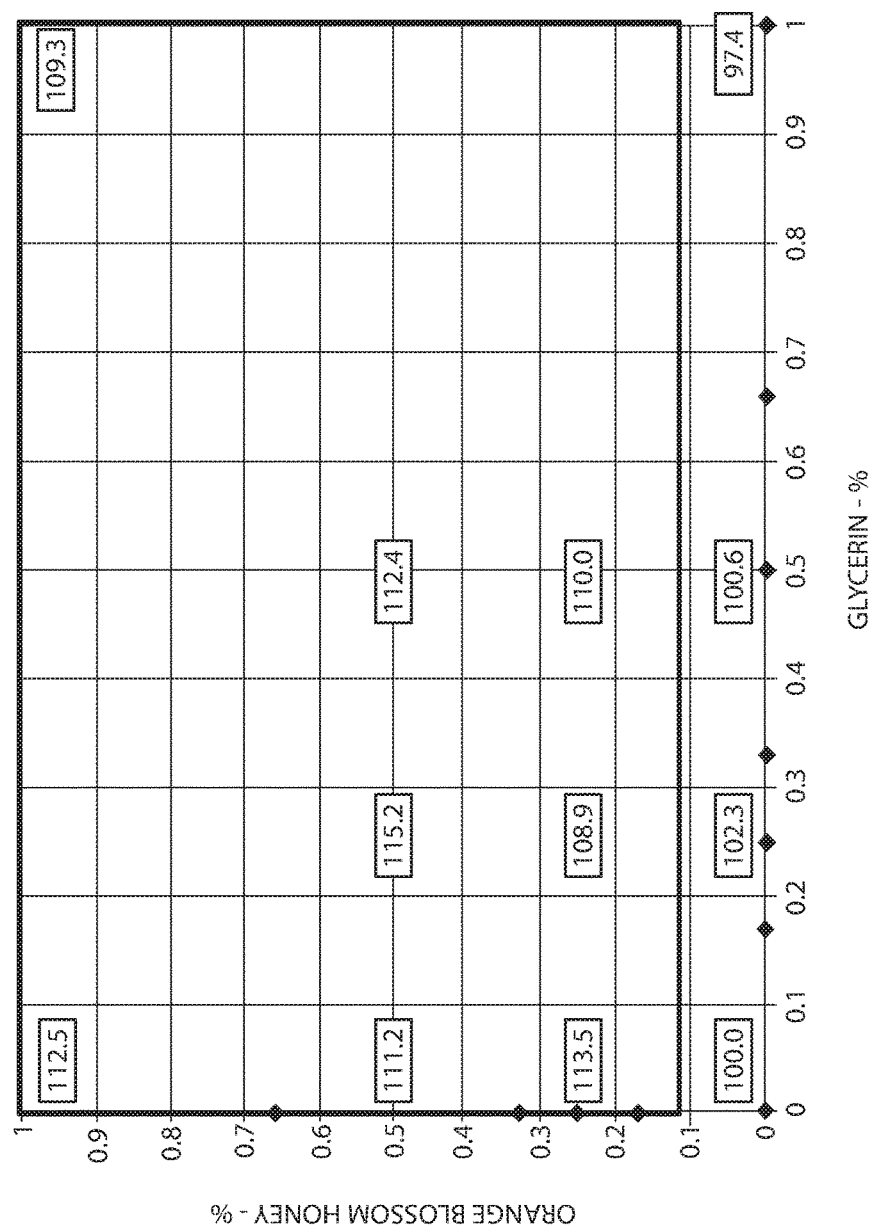
FIG. 4 is a graph illustrating keratinocyte cell growth as measured by cell size utilizing glycerin and/or orange blossom honey—percent change compared to a control.

Further studies indicated that orange blossom honey mitigates the negative effects of glycerin on skin cell growth. As can be seen in FIG. 4, any mixture of orange blossom honey and glycerin shows increased cell growth as measured by cell size and the outlined box is indicative of broad interaction between orange blossom honey and glycerin.

Figure 5:
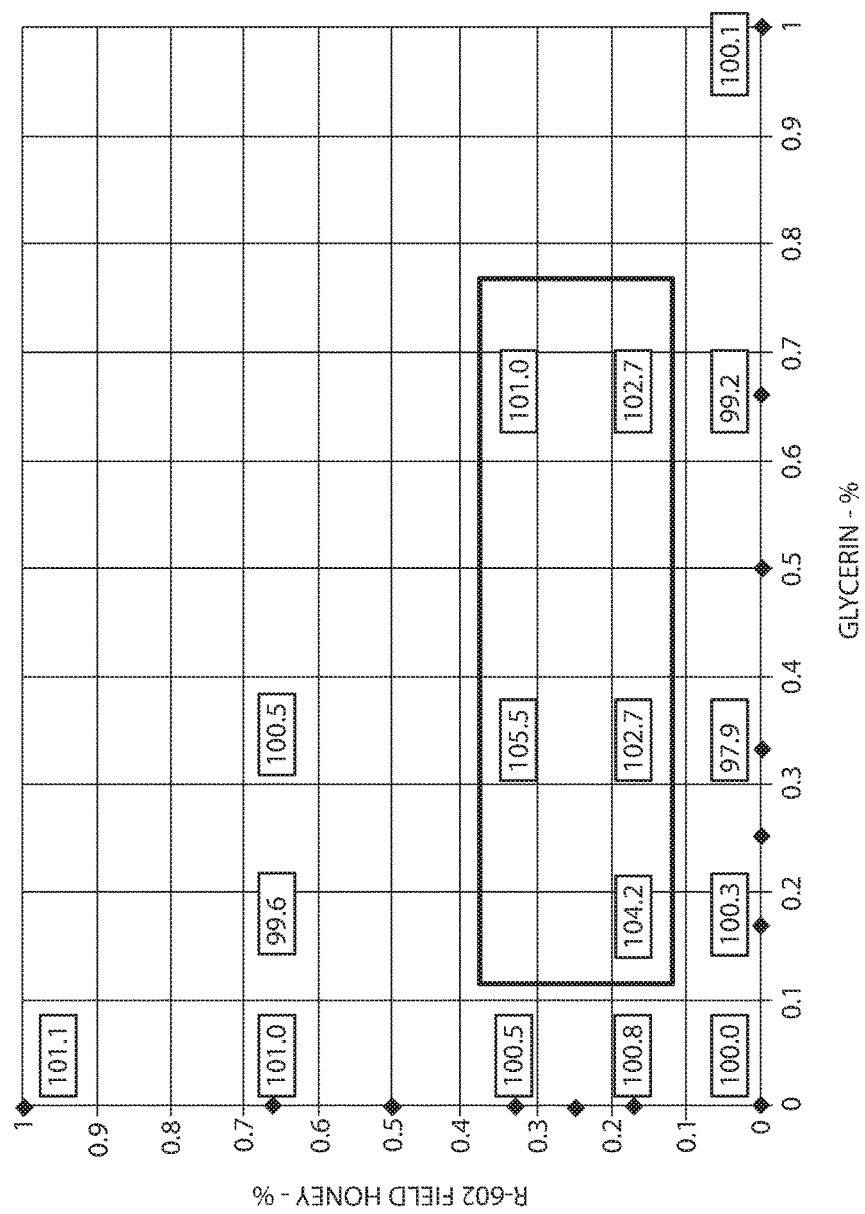
FIG. 5 is a graph illustrating keratinocyte cell growth as measured by cell size utilizing glycerin and/or field honey—percent change compared to a control.
Figure 6:
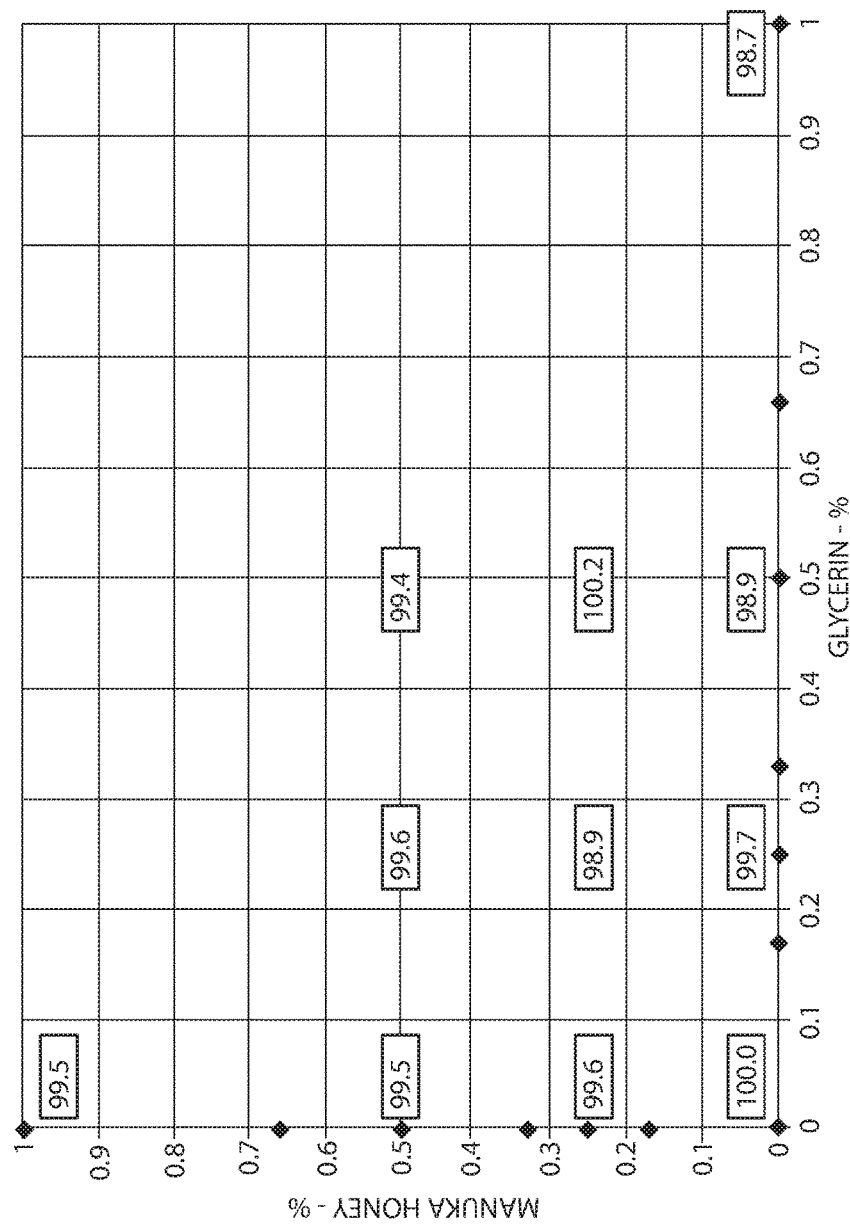
FIG. 6 is a graph illustrating keratinocyte cell growth as measured by cell size utilizing glycerin and/or manuka honey—percent change compared to a control.

The most commonly used honey in skin care, field honey, has little or no effect on glycerin's negative effects as is indicated by the outlined box in FIG. 5. Moreover, the most commonly used honey for beneficial skin care effects, manuka, actually contributes to glycerin's negative skin effects as is shown in FIG. 6.

While the exact ingredients in honey that contribute to the mitigation effects are not precisely known, several possible candidates have been identified by comparative analysis of a number of honey sources. These include the presence of at least one of hesperidin (IUPAC: (2S)-5-hydroxy-2-(3-hydroxy-4-methoxyphenyl)-7-[(2S,3R,4S,5S,6R)-3,4,5-trihydroxy-6-{[(2R,3R,4R,5R,6S)-3,4,5-trihydroxy-6-methyloxan-2-yl]oxymethyl]oxan-2-yl]oxy-2,3-dihydrochromen-4-one), gibberellic acid (IUPAC: (3S,3aS,4S,4aS,7S,9aR,9bR,12S)-7,12-dihydroxy-3-methyl-6-methylene-2-oxoperhydro-4a,7-methano-9b,3-propenoazuleno [1,2-b] furan-4-carboxylic acid) and inositol (IUPAC: (1R,2R,3S, 4S,5R,6S)-cyclohexane-1,2,3,4,5,6-hexol). All three of these compounds have documented bioactive effects. Adverse effects of glycerin on skin cells was previous unknown until this discovery by the inventors, therefore no technology has been conceived or used to mitigate it. As such, the use of specific types of honey, including orange blossom, buckwheat or others containing high levels of hesperidin compared to other types of honey can be used with glycerin in any type of end composition. Examples include, but are not limited to, topical, rinse off or leave on skin care formulations or pharmaceutical or topical drug delivery formulations. Further examples of products comprising the composition of this disclosure are descried below.

Different products comprising the first and second humectants are formulated. These products are illustrated in the following table.

TABLE 1

| Product | First Humectant (approx.) wt. % | Second Humectant (approx.) wt. % | Other Components (remainder) |
|---|---|---|---|
| Hand Cream | 5 | 0.1 | A |
| Body Lotion | 5 | 0.1 | B |
| Body Milk (Lotion) | 2.5 | 0.1 | C |
| Complexion Bar 1 | 8.5 | 0.001 | D, E, F, or G |

TABLE 1-continued

| Product | First Humectant (approx.) wt. % | Second Humectant (approx.) wt. % | Other Components (remainder) |
|---|---|---|---|
| Complexion Bar 2 | 6.75 | 0.001 | E, D, F, or G |
| Complexion Bar 3 | 10.5 | 0.001 | F, D, E, or G |
| Body Wash 1 | 0.5 | 0.1 | H or I |
| Body Wash 2 | 0.5 | 0.01 | I or H |
| Liquid Soap (Concentrated) | 0.5 | 0.1 | J |
| Bar Soap | 7.75 | 0.001 | K |
| Deodorant/Antiperspirant (Roll-on) | 0.01 | 0.01 | L |

The "First Humectant" is USP Glycerin.

The "Second Humectant" is orange blossom honey (food grade, e.g. Grade A).

The "Other Components" make up the remainder of the products, i.e., in addition to wt. % of the First the Second Humectants. These (other) component packages for "A" through "L" are as follows, generally in order of majority to minority ingredient:

A—water, neopentyl glycol diheptanoate, *butyrospermum parkii* (shea) butter, C12-15 alkyl benzoate, caprylic/capric triglyceride, behenyl alcohol, glyceryl stearate, cetyl alcohol, dimethicone, phenoxyethanol, palmitic acid, stearic acid, stearyl alcohol, fragrance, aluminum starch octenylsuccinate, carbomer, lauryl alcohol, lecithin, myristyl alcohol, methylparaben, *cucurbita pepo* (pumpkin) seed oil, propylparaben, sodium hydroxide, xanthan gum, ethylparaben, benzyl salicylate, limonene, linalool, hexyl cinnamal, butylphenyl methylpropional, citronellol, geraniol, alpha-isomethyl ionone, hydroxycitronellal, and coumarin.

B—water, caprylic/capric triglyceride, petrolatum, *butyrospermum parkii* (shea) butter, C12-15 alkyl benzoate, isopropyl palmitate, stearyl alcohol, dimethicone, glyceryl stearate, PEG-100 stearate, sorbitan stearate, phenoxyethanol, cetyl alcohol, fragrance, carbomer, methylparaben, *cucurbita pepo* (pumpkin) seed oil, propylparaben, sodium hydroxide, xanthan gum, ethylparaben, benzyl salicylate, limonene, linalool, butylphenyl methylpropional, citronellol, geraniol, hexyl cinnamal, alpha-isomethyl ionone, and hydroxycitronellal.

C—water, *butyrospermum parkii* (shea) butter, caprylic/capric triglyceride, neopentyl glycol diheptanoate, dimethicone, glyceryl stearate, PEG-100 stearate, phenoxyethanol, cetyl alcohol, fragrance, methylparaben, sodium polyacrylate, butylene glycol, xanthan gum, aloe barbadensis leaf juice, propylparaben, cyclopentasiloxane, ethylparaben, trideceth-6, PEG/PPG-18/18 dimethicone, *vitis vinifera* (grape) seed extract, sorbitol, ascorbic acid, *camellia sinensis* leaf extract, potassium sorbate, sodium hydroxide, sodium benzoate, citric acid, limonene, hexyl cinnamal, benzyl salicylate, linalool, butylphenyl methylpropional, geraniol, citronellol, and citral.

D—sodium palmate, water, alcohol (denat.), sodium cocoate, sucrose, sodium stearate, fragrance, pentasodium pentetate, tetrasodium etidronate, yellow 5, *butyrospermum parkii* (shea) butter, *cucurbita pepo* (pumpkin) seed oil, and red 33.

E—sodium palmate, sodium cocoate, sodium palm kernelate, water, sodium stearate, sorbitol, stearic acid, propylene glycol, fragrance, potassium palmate, sodium chloride, potassium palm kernelate, potassium cocoate, tetrasodium etidronate, potassium stearate, pentasodium pentetate, *cucurbita pepo* (pumpkin) seed oil, *butyrospermum parkii* (shea) butter, yellow 5, and red 33.

F—sodium tallowate, sodium cocoate, alcohol (denat.), water, sucrose, sodium stearate, fragrance, pentasodium pentetate, tetrasodium etidronate, yellow 5, *butyrospermum parkii* (shea) butter, *cucurbita pepo* (pumpkin) seed oil, and red 33.

G—sodium tallowate, sodium cocoate, water, alcohol (denat.), sucrose, sodium stearate, fragrance, pentasodium pentetate, tetrasodium etidronate, yellow 5, and red 33.

H—water, sodium cocoyl isethionate, disodium laureth sulfosuccinate, sodium lauroyl sarcosinate, PEG-150 distearate, cocamidopropyl betaine, sodium chloride, fragrance, glycol stearate, glycereth-26, glycol distearate, polyquaternium-7, PPG-12-buteth-16, hydroxypropyl methylcellulose, tetrasodium ethylenediaminetetraacetic acid (EDTA), butylated hydroxytoluene (BHT), glycol, magnesium nitrate, butylene glycol, citric acid, aloe barbadensis leaf juice, methylparaben, alcohol, methylchloroisothiazolinone, magnesium chloride, propylparaben, *vitis vinifera* (grape) seed extract, sorbitol, propylene glycol, methylisothiazolinone, *perilla ocymoides* leaf extract, phenoxyethanol, ascorbic acid, *camellia sinensis* leaf extract, sodium benzoate, potassium sorbate, ethylparaben, sodium hydroxide, limonene, hexyl cinnamal, benzyl salicylate, linalool, and butylphenyl methylpropional.

I—water, sodium cocoyl isethionate, disodium laureth sulfosuccinate, sodium lauroyl sarcosinate, PEG-150 distearate, cocamidopropyl betaine, glycol distearate, sodium chloride, glycereth-26, fragrance, polyquaternium-7, guar hydroxypropyltrimonium chloride, PPG-12-buteth-16, BHT, *butyrospermum parkii* (shea) butter, *cucurbita pepo* (pumpkin) seed oil, tetrasodium EDTA, citric acid, magnesium nitrate, aloe barbadensis leaf juice, methylparaben, alcohol, methlchloroisothiazolinone, magnesium chloride, propylparaben, propylene glycol, methlisothiazolinone, *perilla ocymoides* leaf extract, sodium benzoate, potassium sorbate, benzyl salicylate, D-limonene, linalool, butylphenyl methylpropional, citronellol, geraniol, hexyl cinnamal, hydroxycitronellal, and alpha-isomethyl ionone.

J—water, sodium cocoyl isethionate, disodium laureth sulfosuccinate, sodium lauroyl sarcosinate, PEG-150 distearate, cocamidopropyl betaine, sodium chloride, glycol stearate, fragrance, glycereth-26, glycol distearate, polyquaternium-7, PPG-12-buteth-16, hydroxypropyl methylcellulose, tetrasodium EDTA, glycol, magnesium nitrate, citric acid, aloe barbadensis leaf juice, *camellia sinensis* leaf extract, methylparaben, *vaccinium myrtillus* fruit/leaf extract, alcohol, methylchloroisothiazolinone, magnesium chloride, propylparaben, methylisothiazolinone, propylene glycol, phenoxyethanol, carrageenan, *perilla ocymoides* leaf extract, sodium benzoate, potassium sorbate, and sea salt.

K—sodium cocoate, sodium palmate, water, fragrance, titanium dioxide, sodium chloride, guar hydroxypropyltrimonium chloride, pentasodium pentetate, tetrasodium etidronate, *vaccinium myrtillus* fruit/leaf extract, butylene glycol, *camellia sinensis* leaf extract, carrageenan, and sea salt.

L—water, aluminum chlorohydrate, propylene glycol diethylhexanoate, stareth-2, stareth-20, fragrance, alcloxa, glycine, bisabolol, camellia sinensis leaf extract, *vaccinium myrtillus* fruit/leaf extract, *zingiber officinale* (ginger) root extract, phenoxyethanol, carrageenan, methylparaben, and sea salt.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "-" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A method of inhibiting moisture loss from skin, said method comprising the step of administering a composition to a subject's skin, wherein the composition comprises:
   I) a first humectant for increasing moisture content of the subject's epidermis; and
   II) a second humectant different from the first humectant for increasing moisture content of the subject's epidermis;
   wherein the second humectant comprises honey capable of inhibiting moisture loss from the subject's epidermis and/or moisture loss from the first humectant when the subject is exposed to dry air conditions;
   wherein the honey is orange blossom honey that is derived from blossoms of the genus *Citrus;*
   wherein the composition is free of honey different from the orange blossom honey; and wherein a combination of the first and the second humectants shows increased cell growth as measured by cell size.

2. The method as set forth in claim 1, wherein the orange blossom honey comprises hesperidin.

3. The method as set forth in claim 1, wherein the orange blossom honey comprises a monofloral honey.

4. The method as set forth in claim 1, wherein a majority of the orange blossom honey is derived from blossoms of the species *Citrus sinensis.*

5. The method as set forth in claim 1, wherein the orange blossom honey is:
   i) selected from the group of raw honey, strained honey, filtered honey, ultra-sonicated honey, or combinations thereof;
   ii) unpasteurized honey; or
   iii) both i) and ii).

6. The method as set forth in claim 1, wherein the second humectant is present in an amount of from about 0.001 to about 99.999 parts by weight based on 100 parts by weight of the composition.

7. The method as set forth in claim 1, wherein the first humectant comprises a sugar alcohol.

8. The method as set forth in claim 1, wherein the first humectant is present in an amount of from about 0.001 to about 99.999 parts by weight based on 100 parts by weight of the composition.

9. The method as set forth in claim 1, wherein the first and second humectants are present in the composition in a weight ratio of from about 12,000:1 to about 1:12,000.

10. The method as set forth in claim 1, wherein the composition is in the form of a topical composition.

11. The method as set forth in claim 1, wherein the subject is mammalian.

12. The method as set forth in claim 1, wherein the composition is substantially free of an occlusive agent different from the first and second humectants.

13. The method as set forth in claim 1, wherein the composition consists essentially of the first and second humectants.

14. A method of inhibiting moisture loss from skin, said method comprising the step of administering a composition to a subject's skin, wherein the composition comprises:
- I) a first humectant comprising glycerol for increasing moisture content of the subject's epidermis; and
- II) a second humectant comprising orange blossom honey that is derived from blossoms of the genus *Citrus* for increasing moisture content of the subject's epidermis;
- wherein the orange blossom honey is capable of inhibiting moisture loss from the subject's epidermis and/or moisture loss from the first humectant when the subject is exposed to air having a relative humidity of no greater than about 50%;
- wherein the orange blossom honey comprises hesperidin, and the composition is free of honey different from the orange blossom honey;
- wherein the first and second humectants are present in the composition in a weight ratio of from about 12,000:1 to about 1:12,000; and wherein a combination of the first and the second humectants shows increased cell growth as measured by cell size.

15. The method as set forth in claim 14, wherein a majority of the orange blossom honey is derived from blossoms of the species *Citrus sinensis*.

16. The method as set forth in claim 14, wherein the composition is completely free of an occlusive agent different from the first and second humectants and wherein the occlusive agent comprises mineral oil.

17. The method as set forth in claim 14, wherein the composition consists essentially of the first and second humectants.

18. The method as set forth in claim 6, wherein the second humectant is present in an amount of from about 0.001 to about 0.1 parts by weight based on 100 parts by weight of the composition.

19. The method as set forth in claim 12, wherein the composition is completely free of an occlusive agent different from the first and second humectants and wherein the occlusive agent comprises mineral oil.

20. The method as set forth in claim 14, wherein the second humectant is present in an amount of from about 0.001 to about 0.1 parts by weight based on 100 parts by weight of the composition.

\* \* \* \* \*